(12) United States Patent
Pearson et al.

(10) Patent No.: US 6,524,619 B2
(45) Date of Patent: Feb. 25, 2003

(54) DOSAGE FORMS USEFUL FOR MODIFYING CONDITIONS AND FUNCTIONS ASSOCIATED WITH HEARING LOSS AND/OR TINNITUS

(75) Inventors: Don C. Pearson, Lakewood, WA (US); Kenneth T. Richardson, Anchorage, AK (US)

(73) Assignee: Chronorx, Inc., Anchorage, AK (US)

( * ) Notice: Subject to any disclaimer, the term of this patent is extended or adjusted under 35 U.S.C. 154(b) by 0 days.

(21) Appl. No.: 09/765,974

(22) Filed: Jan. 19, 2001

(65) Prior Publication Data

US 2002/0061870 A1 May 23, 2002

Related U.S. Application Data

(60) Provisional application No. 60/178,487, filed on Jan. 27, 2000.

(51) Int. Cl.$^7$ .............................. A61K 9/20; A61K 9/24; A61K 9/22
(52) U.S. Cl. .................. 424/472; 424/464; 424/468
(58) Field of Search .................................. 424/468, 472, 424/464, 489, 473, 457

(56) References Cited

PUBLICATIONS

Antolin et al., "Neurohormone–melatonin prevents cell damage: effect on gene expression for antioxidant emzym, es." *The FASEB Journal*, 10(8):882–890 (1996).

Attias et al., "Oral magnesium intake reduces permanent hearing loss induced by noise exposure," *American Journal of Otolaryngology*, 15(1): 26–32 (1994).

Browning et al., "Blood Viscosity as a Factor in Sensorineural Hearing Impairment," *The Lancet*, 1(8473):121–123 (1986).

Choe et al., "A model for amplification of hair–bundle motion by cyclical binding of $Ca^{2+}$ to mechanoelectrical–transduction channels," *Proc. Natl. Acad. Sci. USA*, 95: 15321–15326 (1998).

Cruickshanks et al., "Prevalence of Hearing Loss in Older Adults in Beaver Dam, Wisconsin," *Am. J. Epidemiol.*, 148(9): 879–886 (1998).

Dubreuil, "Essai therapeutique dans les surdites cochleaires aigues," *La Presse Medicale*, 15(31): 1569–1561 (1986).

Hudspeth, "The Cellular Basis of Hearing: The Biophysics of Hair Cells," *Science*, 230(4727):745–752 (1985).

Ikeda et al., "Evaluation of Vitamin D Metabolism in Patients with Bilateral Sensorineural Hearing Loss," *Am. J. Otol.*, 10(1):11–13 (1989).

Lamm, "Noise–induced cochlear hypoxia is intensity dependent, correlates with hearing loss and precedes reduction of cochlear blood flow," *Audiol Neurootol*, 1: 148–160 (1996).

Luscher et al., "Local regulation of the coronary circulation in health and disease: role of nitric oxide and endothelin" *European Heart Journal*, 16(Suppl C):51–58 (1995).

Nakai and Masutani, "Noise–induced Vasoconstriction in the Cochlea," *Acta Otolaryngol Supp.*, 447:23–27 (1988).

Ravecca et al, "Ipoacusia neurosensoriale progressiva: cause metaboliche, ormonali e vascolari," *Acta Otorhinolaryngol Ital Suppl.*, 59: 42–50 (1998).

Ubbink et al.: "Vitamin Requirements for the Treatment of Hyperhomocysteinemia in Humans$^{1,2}$," *J. Nutrition*, 124(10):1927–1933 (1994).

Yamasoba et al., "Role of glutathione in protection against noise–induced hearing loss," *Brain Research*, 784: 82–90 (1998).

*Primary Examiner*—James M. Spear
(74) *Attorney, Agent, or Firm*—Townsend and Townsend and Crew LLP

(57) ABSTRACT

The invention defines interdependent biofactors and biomolecules, and clinically useful formulations that are comprised of them. The active agents are demonstrated to be complementary in their physiologic functions especially as these relate to the quenching of free radicals and to the support of endothelial physiology, the reduction of hyperinsulinemia and improvements in vascular health. The active components of the invention are selected for inclusion in precise combinations specifically because they improve these various conditions and physiological functions, and by so doing reduce a variety of risks associated with hearing loss and tinnitus. The resulting enhancement of general systemic vascular health, improvement in local VIII$^{th}$ nerve vascular health, modulation of conditions surrounding blood fluid dynamics, the consequences of hyperinsulinemia, and improvements in free radical defenses, all reduce the potential for cochlear hair cell death and VIII$^{th}$ nerve atrophy, and the hearing loss and possible deafness that accompany them.

14 Claims, No Drawings

DOSAGE FORMS USEFUL FOR MODIFYING CONDITIONS AND FUNCTIONS ASSOCIATED WITH HEARING LOSS AND/OR TINNITUS

CROSS REFERENCE TO RELATED APPLICATION

This application is related to United States Provisional Patent Application No. 60/178,487, filed Jan. 27, 2000, and claims all benefits legally available therefrom. Provisional Patent Application No. 60/178,487 is hereby incorporated by reference for all purposes capable of being served thereby.

BACKGROUND OF THE INVENTION

1. Field of the Invention

This invention is in the field of pharmacology and relates specifically to the improvement of clinical conditions associated with symptomatic or presymptomatic hearing loss and/or tinnitus and the reduction of risks associated with their onset.

2. Description of the Prior Art

Pertinent Anatomy of the Ear

The ear of humans consists of three parts: the outer, middle and inner ear. The outer ear consists of the external ear and the auditory canal. The external ear modifies sound waves and the air-filled auditory canal conducts the sound waves to the middle ear, which consists of the tympanic membrane, or eardrum; the eustachian tube; and three tiny bones called the hammer, anvil, and stirrup. Membranes and bone surround the middle ear with the eustachian tube connecting it to the pharynx, equalizing the air pressure between the middle ear and the atmosphere.

Within the middle ear, sound first vibrates the tympanic membrane, which in turn vibrates the hammer, the anvil, and the stirrup. These bones transmit vibrations from the tympanic membrane to a much smaller membrane, the oval window. The oval window covers the opening of the inner ear, in which sound vibrations are transmitted through fluid. The fluid-filled hollow bones of the inner ear form the spiral shaped cochlea and the vestibular apparatus where vibrations are translated into neural signals.

The senses of hearing and equilibrium depend on sensory receptors called hair cells located on the basilar membrane of the cochlea. These hair cells can detect motions of atomic dimensions and respond more than 100,000 times a second. Biophysical studies suggest that mechanical forces control the opening and closing of transduction channels by acting through elastic components in each hair cell's mechanoreceptive hair bundle. Other ion channels, as well as the mechanical and hydrodynamic properties of hair bundles, tune individual hair cells to particular frequencies of stimulation.

Even though well characterized at a biophysical level, the mechanical transduction mechanism of hair cells is still not completely understood in molecular terms. This discrepancy is in part due to the extreme scarcity of hair cells; instead of the millions or even hundreds of millions of receptor cells that the olfactory and visual systems possess, only a few tens of thousands of hair cells are found in the internal ears of most vertebrate species. The small number of hair cells and the direct transduction mechanism has greatly impeded molecular biological and biochemical characterization. Molecular description of hair-cell transduction has consequentially lagged behind description of vision and olfaction.

A comprehensive model for hair-cell transduction has emerged. Residing in the mechanoreceptive organelle of a hair cell, the hair bundle (the transduction apparatus) consists of at least three components: the transduction channel, a mechanically gated ion channel; the tip link, an extracellular filament that transmits force to the channel's gate; and the adaptation motor, a mechanism that maintains an optimal tension in the tip link so that the channel can respond to displacements of atomic dimensions.

The tip link appears to be the anatomical correlate of a gating spring, an elastic element through which stimulus energy can affect the transduction channel. A cluster of myosin molecules constitutes the adaptation motor. Hair cells express a variety of myosin isozymes.

The specialized innervation of hair cells makes the restoration of hearing potentially a practical form of neural-replacement therapy. Hair cells lack axons and dendrites; instead, the basolateral surfaces of these cells make afferent synaptic contacts with VIIIth nerve terminals and receive efferent contacts from neurons in the brainstem. When hair cells are destroyed, this innervation often remains intact; indeed, the integrity of the afferent innervation underlies the success of cochlear prosthetics. If hair cells can be successfully regenerated, it follows that their re-innervation may be possible. In contrast, in other proposed neural-replacement therapies, transplanted neurons are called upon to extend their axons substantial distances in order to make appropriate connections. It is questionable whether such axiogenesis is possible in the adult brain or spinal cord.

Axons in the cochlear component of the VIIIth VIIIth nerve project to each of the three cochlear nuclei; an orderly representation of stimulus frequency is preserved at each subsequent level of the ascending pathway. Extensive decussation occurs at the pontine and midbrain levels. Then, via the superior olivary nuclei process, information is transmitted to an auditory spatial map in the inferior colliculus and finally via the medial geniculate nucleus to the temporal cerebral cortex.

Pertinent Physiology of the Ear

The defining event in the hearing process is the transduction of mechanical stimuli into electrical signals by hair cells, the sensory receptors of the internal ear. Stimulation results in the rapid opening of ionic channels in the mechanically sensitive organelles of these cells, their hair bundles. These transduction channels, which are non-selectively permeable, are directly excited by hair-bundle displacement. Hair cells are selectively responsive to particular frequencies of stimulation, due to both the mechanical properties of their hair bundles and because of an ensemble of ionic channels that constitutes an electrical resonator.

The unique structural feature of the hair cell is the hair bundle, an assemblage of microscopic processes protruding from the cell's top or apical surface. Each of these processes, which are termed stereocilia, consists of a straight rod of fasciculated actin filaments surrounded by a membranous tube. Because the microfilaments are extensively cross-bridged, each stereocilium behaves as a rigid rod. When mechanically disturbed, it remains relatively straight along its length but pivots about a flexible basal insertion. When the fluid moves in response to sound, the force of viscous drag bends the bundles, thereby initiating a response.

At any instant, each transduction channel at a stereocilium's tip may be either closed or open. The relative values of the rate constants for channel opening and closing determine the fraction of the transduction channels open in the undisturbed steady state. When the hair bundle is deflected with a positive stimulus, the values of the rate constants are altered; the opening rate constant is larger and the closing rate constant smaller than the original values. The new steady-state transduction current is therefore greater and the cell is depolarized. Pushing the hair bundle in the opposite direction has a contrary effect on the rate constants, culminating in a hyperpolarizing response.

When the hair bundle is deflected, transduction channels open and positive ions, largely $K^+$, enter the cell. The depolarization evoked by this transduction current activates voltage-sensitive $Ca^{2+}$ channels. As $Ca^{2+}$ ions flow into the cell they augment depolarization and raise the intracellular concentration of $Ca^{2+}$, especially the local concentration just beneath the surface membrane. Elevated $Ca^{2+}$ concentrations activate $Ca^{2+}$-sensitive $K^+$ channels. As $K^+$ exits through these pores it initiates membrane repolarization and diminishes the activation of $Ca^{2+}$ channels. The fluid bathing the apical surface of a hair cell characteristically has a much higher $K^+$ concentration than that contacting the basolateral surface; as a consequence, $K^+$ can both enter and leave the cell passively. Once the membrane potential becomes more negative than its steady-state value, intracellular $Ca^{2+}$ concentration is reduced by sequestration of the ion within cytosolic organelles and by extrusion through $Mg^{+}$-cofactored, ATPase-fueled ion pumps. The $Ca^{2+}$-sensitive $K^+$ channels have now closed and the hair cell returns to its initial condition.

Hearing Loss and/or Tinnitus—The Disease

Prevalence and Socioeconomic Impact

Society is awakening only slowly to the cost of acoustic trauma in both industrial and recreational settings. Within the next decade or two, the Walkman® generation will find itself unexpectedly interested in auditory pathophysiology. Varying degrees of deafness affect about 30 million Americans and cost the nation over $56 billion annually (Dana Alliance for Brain Initiatives, 1996).

In a population-based study of 3,753 residents in Beaver Dam, Wis., the prevalence of hearing loss in adults aged 48–92 years, was 45.9%. The average age of participants was 65.8 years. The hearing loss increased with age and was greater for men than women. The prevalence of hearing loss is a striking 95 percent in the 80+ year age group, which translates into an increasing problem in nursing homes.

Hearing loss is a growing problem in occupational health, including the military wherein about one-third had hearing loss by the end of basic training. Hearing loss is evident even when precautions are taken.

Tinnitus is also increasingly common (about 15% of adults#17923]) and is often an early indicator of existing or future hearing loss. This hearing loss is ordinarily permanent, for cochlear hair cells are not replaced by mitotic turnover. Although cochlear prostheses have now restored partial hearing to some 15,000 deaf individuals worldwide and researchers continue to seek a means of overcoming deafness by the replacement of hair cells, improved prevention represents the most reasonable present approach.

Pathophysiology of Hearing Loss and/or Tinnitus

Hearing loss may occur acutely due to hair cell trauma from excessive $Ca^{2+}$ signaling and generation of reactive oxygen species (ROS) from noise exposure. Chronic progressive hearing loss is often associated with labyrinthine ischemia from either hematologic disturbances (e.g., increased blood viscosity, decreased red blood cell deformability) or from non-hematologic vasoconstriction due to progressive vascular endothelial dysfunction. Chronic neurosensory hearing loss accompanies aging and is more common in the diabetic population.

I. Acute Hair Cell Trauma

Noise-induced trauma to the hair cells is sound-intensity dependent and can lead to hair cell death. Since mitotic hair cell replacement does not occur, traumatic hearing loss is permanent. The pathophysiology of traumatic hair cell loss is multivariable. Hypoxia, excessive $Ca^{2+}$ signaling, vasoconstriction, intracellular energy exhaustion, ROS and ROS and excitotoxicity, each contribute individually and as a detrimental synergistic composite.

As previously stated, when the hair bundle is deflected transduction channels open and activate voltage-sensitive $Ca^{2+}$ channels. $Ca^{2+}$ inflow into the cell causes depolarization. At the same time, however, as the intracellular concentration of $Ca^{2+}$ rises —especially its local concentration just beneath the surface membrane of the hair cell—these high $Ca^{2+}$ concentrations activate $Ca^{2+}$ sensitive $K^+$ outflow channels; an energy requiring activity supported by $Mg^{2+}$-cofactored ATPase. As $K^+$ exits, membrane repolarization begins and closes the $Ca^{2+}$ channels. Once the membrane potential is somewhat more negative than its steady-state value, intracellular $Ca^{2+}$ concentration is further reduced by sequestration of the ion within cytosolic organelles and by its continuing extrusion through $Mg^{+-}$ cofactored, ATPase-fueled ion pumps.

Shear stress is increased by vasoconstriction (inter alia) and increased shear stress raises $Ca^{2+}$ channel permeability as much as ten or twelve fold. Since $Ca^{2+}$ influx augments the endothelin-1-induced vasoconstrictive effect of pooled intracellular $Ca^2$, a "circle-in-a-spiral" vasoconstrictive effect occurs. The components of this patent, operating in concert, untie this metaphorically tangled biologic shoelace.

This complex physiology of hearing can become overwhelmed by high intensity and/or prolonged sound. Energy for hearing is supplied by mitochondria which are only 95% efficient in their use of oxygen; 5% of oxygen ends up as potentially damaging ROS. Furthermore, excessive hearing demands result in excessive oxygen requirements that, in turn, lead to hair cell hypoxia. This situation is further exaggerated by local vasoconstriction resulting from ROS-induced, endothelial cell dysfunction. Excessive energy requirements exhaust the ability of the cells to extrude $Ca^{2+}$; as a result, $Ca^{2+}$ pools intracellularly and as long as the intense sound continues it continues to pour into the cell (see above). Excess intracellular $Ca^{2+}$ leads to the production of endothelin-1 (ET-1), which has a prolonged and intense vasoconstrictor action, exaggerating the effect of hypoxia and delaying hair cell recovery. Of course, the hair cell may go on to die, not to be replaced.

Enzymes involved in maintaining glutathione (gamma-glutamyl-cysteinyl-glycine (GSH in the reduced state) protect hair cells from ROS-induced damage. This suggests that agents that protect or augment the GSH system in the cochlea may be protective against noise-induced hearing loss.

Cochlear ischemia (which is discussed at length later) and acoustic trauma result in an immediate hearing loss accompanied by the complete disruption of the terminal dendrites of primary auditory neurons postsynaptic to the sensory inner hair cells (IHCs). This synaptic uncoupling is due to an acute glutamate (IHC neurotransmitter) excitotoxicity process. However, some repair is possible: twenty-four hours after an excitotoxic injury the inner hair cells may be contacted by postsynaptic dendrites and cochlear function may recover partially. Neo-synaptogenesis may be complete 5 days post exposure and this type of functional recovery probably accounts for most restored hearing after temporary losses due to excitotoxic-related pathologies.

Cellular Defenses Available for Acute, Sound-induced Hair Cell Trauma

1. Regulate the Passive Transfer of $Ca^{2+}$ into the Hair Cell and Optimize the $Ca^{2+}$ Extrusion Pump Adequate $Mg^{2+}$ is critical for both of these defense activities: a) it functions as a competitive, passive $Ca^{2+}$ channel "blocker"; b) it is the required cofactor for the ATPase-catalyzed, $Ca^{2+}$ extrusion pump; c) it is required as a cofactor for the mitochondrial enzymes involved in any exaggerated energy production mandated in the hair cell by intense sound. For these reasons adequate $Mg^{2+}$ is necessary for hair cell defense. Hypomagnesemia is associated with hearing loss from sound-induced hair cell trauma, but the latter can be reduced by supplementation with oral $Mg^{2+}$. Hypomagnesemia is commonly present in the aging and in diabetic populations and contributes to the fact that each of these groups is more prone to sound-induced hair cell and efferent synapse damage.

Although glutathione peroxidase (GSHPx) levels, necessary for the intracellular synthesis of GSH, appear naturally to rise with aging, reflecting a compensatory increase in the GSH needed to counter the rising levels of ROS associated with increasing age, intracellular GSH remains low in the presence of hypomagnesemia.

There is evidence that ginkgo biloba is also helpful in reducing acute sound induced hair cell trauma, perhaps relating to its vasodilatative effect. Given the importance of maintaining the normal state of vascular mid-dilatation and the sudden requirement for this at the time of noise trauma the effectiveness of ginkgo biloba is and therefore its inclusion in this patent is understandable.

2. Improve the Multilayered, Coordinated, Intracellular Molecular Defenses Against ROS ROS are produced by intense sound and contribute to hair cell trauma by a variety of etiologies including: a) immediately traumatic intracellular events, b) induced vasoconstriction and c) excitotoxic (glutamate) destruction of the terminal dendrites of primary auditory neurons postsynaptic to the sensory inner hair cells.

Intracellular defenses against the destructive effects of ROS require a number of components functioning as a team, including: 1) the GSH/GSHPx system which maintains production and optimizes its catalytic functions (e.g., cysteine, melatonin, riboflavin, selenium); 2) sulfhydryl contributors that reduce the ROS "load" on the GSH/GSHPx system (e.g., lipoate, taurine) and 3) molecules involved in ROS scavenging (e.g., D, alpha-tocopherol, ascorbate).

These ROS scavengers function as an interdependent, dynamic intracellular ensemble. Endogenous peptides like GSH and GSHPx play the predominant role in many regulatory processes, usually with high specificity and potency, and rapid degradation; the latter is necessary for flexible regulation.

Such a system requires a healthy means of rapid regeneration and maintenance of adequate levels of complementary components. E.g., it is well established that once D, alpha-tocopherol has functioned as a reductant of ROS—preventing lipoproteins from being oxidized, endothelial cells from becoming dysfunctional and DNA from being damaged—it exists in an oxidized form, tocopheroxyl. Ascorbate, in turn, acts as a reductant of tocopheroxyl and rejuvenates alpha tocopherol, but in the process is itself oxidized to a prooxidant, dehydroascorbate. Finally, GSHPx, activated by its cofactor selenium and utilizing reduced GSH as its substrate, completes the cycle and rejuvenates ascorbate. (These activities emphasize the often-overlooked fact that many antioxidants like ascorbate and alpha tocopherol can be driven into prooxidant states. It importantly defines how imperative it is to maintain a balanced, synergetic intracellular milieu and avoid artificially converting a cellular physiologic state into one that is pathologic.)

Lipoate (thioctic acid), another potent antioxidant, is also regenerated through redox cycling and raises intracellular GSH levels by providing thiols. Since GSH (a thiol-requiring antioxidant) cannot effectively be taken orally (see below) while alpha-lipoic acid can, the latter is effective as a dietary supplement in maintaining intracellular GSH levels.

GSH levels cannot be raised directly by supplemental administration in the diet because it is produced intracellularly from the amino acids glutamic acid, cysteine and glycine; cysteine is the functional component. As the functional unit of GSH, cysteine can be supplied effectively by providing a GSH prodrug, such as N-acetyl-cysteine (NAC), 2-oxothiazolidine-4-carboxylate (OTC) or mercaptopropionylglycine (MPG). In fact, the GSH prodrug OTC has been shown rapidly to restore GSH when the latter is acutely depleted.

$Zn^{2+}$ is a necessary trace element in GSH synthesis, as is $Mg^{2+}$.

GSH presence in the brain is enhanced by pineal melatonin via this neurohormone's ability to increase the mRNA of GSHPx.

In appropriate doses in sequence and in concert, these several components - D, alpha-tocopherol, ascorbate, lipoate, GSH, NAC, OTC, MCG, $Zn^{2+}$, selenium and melatonin—function efficiently to reduce the cell damaging effect of ROS while avoiding the cell damage that each can exert should they accumulate in their prooxidant form.

In summary:

An important etiology of hearing loss from acoustic over stimulation is the generation of ROS. Those ROS not removed by limited, resident antioxidant defenses cause significant damage to the sensory cells of the cochlea. Studies have shown that GSH inhibition increases the susceptibility of the cochlea to noise-induced damage and that replenishing GSH by the administration of the GSH prodrug OTC, presumably by enhancing the availability of cysteine (thiols), attenuates noise-induced cochlear damage.

Intracellular hair cell GSH is reduced when oxidant stress is increased to a level that depletes or disorganizes inherent, multilayered intracellular ROS defense systems. As a defense, GSH synthesis is markedly and selectively up regulated in the lateral wall by noise exposure (which imposes a higher requirement for the components required for synthesis). This up-regulation, presumably, is in response to the robust consumption of GSH as it is over-utilized in scavenging elevated, noise-induced, toxic levels of ROS.

There is a rise in GSHPx levels with aging; presumably merely to compensate for the increased amounts of GSH required to counter elevated, universal levels of ROS.

Unfortunately, GSH is often reduced because of hypomagnesemia, also common in the aged. These facts underline the particular importance of supplementing $Mg^{2+}$ in an aging population to maintain appropriate intracellular synergetics for resisting sound-induced hearing loss.

Alpha-tocopherol, ascorbate, selenium and $Mg^{2+}$ are commonly deficient even in average diets. These components, GSH prodrugs and lipoic acid must be supplemented orally to meet the ROS hair cell defense demands of intense or prolonged sound exposure and the depredations of aging. The same is true for melatonin, which may be progressively reduced during aging either because of increased intracellular ROS demands, inadequate pineal production or both.

II. Chronic Labyrinthine Ischemia

Progressive sensorineural hearing loss (PSNHL) is often caused by chronic labyrinthine ischemia, either from by hematologic factors (blood viscosity and/or rigidity of the red blood cells) or non-hematologic factors (tissue perfusion pressure, blood vessel diameter).

A. The Synergetics of blood Flow are Nonlinear

The nonlinear synergetics of blood rheology may shift rapidly causing abrupt reductions in flow and result in acute, localized loss of tissue perfusion and cell death. These may be associated with immediate hearing loss and cell damage. The latter may contribute continuously to PSNHL. This pathology is a pulsed, progressive, permanent and yet preventable disability.

That these phase shifts in blood rheology, with their associated changes in available oxygen and nutrients, can be sound induced and cause permanent hearing loss has been established. That they can be prevented is one basis for this patent.

The patterns inherent in the nonlinear dynamics of blood flow have valuable clinical implications for both the acute, traumatic hearing loss described above and for the chronic progressive hearing losses relating to chronic labyrinthine ischemia.

There is a strong and complex association between aspects of blood rheology and hearing impairment. These must be understood.

Two separate items are strongly associated with sensorineural hearing impairment: a) bulk Theological properties of blood and b) the Theological properties of individual red blood cells (RBCs, erythrocytes). Bulk flow abnormalities appear to be more important at lower frequencies, while defects in RBC deformability are more detrimental to higher frequency hearing.

B. Erythrocytes and the Concept of Flow Synergetics

1. Deformability

Erythrocytes are the simplest cells in the human body. Formed as nucleated cells in the bone marrow, erythrocytes lose this element before their release into general circulation. Once in the circulation, an RBC assumes the shape of a biconcave disk. These non-nucleated cells have a changeable (dynamic) fluidity in flowing blood.

Cellular deformability is influenced by three distinct cellular components: a) cell shape, which determines the ratio of cell surface to cell volume; b) cytoplasmic viscosity, which is regulated by intracellular hemoglobin concentration; c) membrane properties including shear, negative surface charge (sialic acid) and the coefficient of surface viscosity.

The biconcave disk shape of normal erythrocytes creates an advantageous surface-to-volume ratio that allows the erythrocyte to undergo marked deformation while maintaining a constant surface area. Concurrently the extensive surface-to-volume ratio enhances respiratory gas exchanges in the lungs and in the peripheral circulation. Maintenance of deformability is essential for these cells to negotiate successfully small passageways in the microcirculation. Erythrocytes, which have a diameter of 8 $\mu$m, can squeeze through interendothelial slits of 0.5 $\mu$m without rupture. This incredible, reversible deformability is permitted by the presence of a flexible cytoskeleton of interconnected filamentous proteins anchored to the inner part of the plasma membrane.

2. Cell Membranes

Like other cellular membranes, that of the erythrocyte is a selectively permeable lipid barrier with specific ion pumps, channels and gates.

The deformability of the erythrocyte membrane is determined by lipid-protein interactions. There are three types of membrane lipids: phospholipids, cholesterol and glycolipids. The phospholipids form a membrane bilayer with hydrophilic groups oriented towards the exterior and hydrophobic hydrocarbons oriented towards the interior. About half of the membrane lipids are phospholipids, about half cholesterol lipids. The most important interacting membrane protein is glycophorin that makes up 75% of all erythrocyte membrane proteins.

3. Fluid Dynamics

Any solid particle suspended in a shearing fluid is rotated by the flow characteristics imposed by viscous drag. Solid spheres are driven into continuous rotation while irregularly shaped particles (e.g., solid ellipsoids like rigid RBCs) are driven into irregular movements. Although a fluid droplet may be spherical at rest it is progressively deformed into a prolate ellipsoid as shear rates rise. Its major axis then becomes oriented more or less parallel to the direction of flow. In addition, the deformed fluid droplet acquires the rotational movement of the suspending fluid, which minimizes the consequences to it of gyrations encountered during shearing: a) droplet (cellular) aggregation, crowding and collisions are markedly reduced and b) entropy generation is minimized.

These phenomena variably occur in any sheared suspension of RBCs. When subjected to physiologically high shear stresses the highly flexible RBCs behave like liquid droplets and blood undergoes a phase transition into a highly fluid emulsion. At low rates of shear these same cells behave more like quasi-elastic, semi-solids. In summary: RBCs at normal, relatively high physiologic levels of shear behave much more like a fluid than a solid: hence the term Shear-Induced Fluidality (SIF) to designate their behavior.

SIF can be explained by several features of erythrocyte mechanics: a) these cells consist of a flaccid membranous bag incompletely filled with a concentrated, very fluid solution of cytosolic macromolecules, b) the cytoplasm convectively mixes oxyhemoglobin between the cytosol and the plasma, movement that markedly accelerates oxygen uptake and release, c) unique intra-cytosolic laminar flow is induced by rotational slippage of the RBC membrane around the cytosol (called "tank treading"); this membrane movement is driven by surrounding shear forces.

When blood is properly driven, SIF spontaneously enhances its fluidity so that the cellular elements (RBCs, white blood cells, (WBCs), et al) can easily negotiate small vessels despite the fact that resting capillaries are substantially smaller in diameter than they.

Physiological or pathological changes in the dynamics of blood flow associated with these processes responsively can induce sudden, non-linear changes of flow and fluidity.

At rest (zero shear) human RBCs regularly combine into rouleaux and three-dimensional networks of rouleaux.

At low shear rates between 0.01 and 10/s viscidation is increased by RBC aggregation.

At high shear rates between 10 and 1000/s fluidity is improved by changes in RBC orientation and deformation (see above).

As one proceeds from stationary to rapidly moving blood flows, progressive increases in dispersion and deformation of the RBCs lead to changes in the appearance and the behavior of the blood: from a viscous suspension to an emulsion-like, self-lubricating fluid.

Phase jumps from slow movement associated with aggregation, to rapid movement associated with dispersion and deformation can occur—a circular causality, wherein causes and consequences are inseparably intertwined. Although at normal physiological high flow rates these dynamics permit an efficient coordination of perfusion, the opposite will occur in slowly moving blood, which phase shifts into a self-viscidizing mode once the shear stresses fall below a critical level. The perfusion pattern has now become chaotic, entropic, and nonlinear.

In all segments of the normal macro and microvasculature, both the shear rates and the shear stresses are high, in the order of magnitude of 100–1000/s and vary inversely to the vessel diameter. The controlling parameter is the intravascular pressure: When the local vascular pressure drops sufficiently to reduce shear forces, the low-flow behavior of increasing cellular aggregation and increasing viscidation begin leading to strongly disordered flow patterns.

The above admittedly lengthy explanation helps explain why vasoconstriction (using this term in its broadest sense and developed more extensively below) caused by either intense/prolonged sound or chronic labyrinthine ischemia diminishes the physiological defenses necessary for the preservation of blood fluidization and greatly increases the probability of a local, auditory, nonlinear phase jump toward chaotic, cellular aggregation. The result is otherwise preventable auditory tissue damage. The prevention of the latter is the focus of this invention.

C. Vasoconstriction

1. Microvascular Regulation

Disturbed microvascular regulation and its resulting vasoconstriction create disastrous phase shifts in blood flow that are integral to auditory damage and hearing loss.

A balanced biochemical relationship between nitric oxide (NO) and ET-1 mediates local blood flow and many other facets of systemic vascular tone.

NO is a highly soluble gas formed within endothelial cells by the action of the constitutive enzyme nitric oxide synthetase (eNOS). NO activates guanylate cyclase and increases guanosine monophosphate (cGMP) within the vascular musculature. In turn, cGMP produces relaxation and dilatation of the vessel. NO is the most powerful initiator of vasodilation known, except for histamine.

Furthermore, its continuous constitutive production maintains the normal vascular system in a physiologic state of partial vasodilation. Importantly, in an aging population increasingly affected by hearing loss and in whom atherosclerosis is universal, the ability of the vascular endothelium to produce NO is lessened because of reduced local levels of eNOS.

ET-1 is also formed within and secreted by endothelial cells. ET-1 reacts with local receptors on smooth muscle cells to produce a powerful and long-lasting vasoconstriction. Aged or unhealthy endothelial cells particularly release ET-1, e.g., in the presence of atherosclerosis or in the presence of locally bound aggregates of endothelial leukocytes or platelets. The smooth muscle contraction produced by ET-1 strongly opposes the vascular smooth muscle cell (VSMC) relaxation of NO. This causes spotty or widespread vasoconstriction of the small vessels of the cochlea with resulting local hypoxia and hair cell atrophy.

This critical balance between constitutive NO and ET-1 mediates the regulation of blood flow within the auditory microvasculature.

2. Vascular Disease

Localized vascular disease can exist in a variety of forms and result in a variety of pathological clinical conditions including chronic labyrinthine ischemia, which eventually result in hearing loss. All are associated with a reduction of oxygen delivery to surrounding, dependent tissues. In the ear there are two tissues particularly vulnerable to hypoxia:

a. The hair cells of the cochlea.

b. The afferent dendrites of the VIIIth nerve. These dendrites are vulnerable to damaging excitotoxicities that result from the excessive release of glutamate at the synapse after intense/prolonged sound. (Hypoxia and ROS reduce available GSH, which is necessary to maintain glutamate below exorbitant excitotoxic levels. (See discussion above)

A reduction in cochlear oxygen delivery may follow acute or chronic, segmental or widespread vascular spasm or prolonged vasoconstriction secondary to a physical or functional reduction in the vascular lumen. This luminal reduction may be caused by or be associated with hypertrophy of the vascular muscle wall (the media), the accumulation of atherosclerotic plaque, platelet agglutination, RBC rigidity, disturbed laminar flow, blood fluidity or local inflammatory swelling and leukocytic accumulation. Any and all of these often occur with aging or in association with other systemic disease: diabetes, hypertension, dyslipogenesis, hyperinsulinemia, arteriosclerosis, thyroid disease, etc. Although vascular insufficiency at specific tissue sites is widely variable and not predictable with certainty, the fact that most patients with hearing loss are over 45 years old makes the frequency of these risk factors and the frequency of vascular insufficiency, high in this clinical group.

Any proposed therapy should attempt to reduce the negative influences of the above general risk factors and reduce local cochlear vascular insufficiency, in addition to reducing noise exposure. For example: A therapeutic reduction of those endothelial abnormalities which contribute to (or are created by) risk factors which compromise local vascular integrity, will reduce the potential for cochlear hair cell failure where microvascular dysregulation or vasoconstriction is significant. If a reduction of vascular risk factors is united with a reduced exposure to noise, the combined effects of a well-oxygenated hair cell and lessened excitotoxicity of VIIIth nerve dendrites will reduce progressive hearing loss.

D. Insulin Resistance and Diabetes Mellitus

Tobacco smoking, obesity, high fat diets and increasing age are all associated with elevations of tumor necrosis factor alpha (TNF-α) and an increased incidence of diabetes mellitus type 2 (NIDDM). TNF-α elevations and NIDDM are both closely associated with hyperinsulinemia and reduced insulin sensitivity. Hyperinsulinemia and reduced insulin sensitivity, which may exist in 25% of an otherwise apparently healthy general population, are associated with disturbed vascular laminar flow, endothelial dysfunction, dyslipogenesis and hypertension—in brief, with vascular insufficiency, vasoconstriction and reduced deformability of RBCs. The hearing loss and tinnitus population is predominantly represented by an older age group and which is not immune to the existence of smoking, obesity, NIDDM, background levels of hypertension, etc. The epidemiological relationships that exist between diabetes, aging and neurosensory hearing loss has been discussed above.

SUMMARY OF THE INVENTION

The present invention resides in pharmaceutical preparations for use as oral dosage forms or transmembrane delivery forms. The preparations contain specific therapeutic biofactors and biomolecules selected because of their particular and critical physiological effects. These are combined in highly defined groups and amounts to achieve maximum complementarity of action.

This invention prevents hair cell damage, VIIIth nerve dendritic damage, labyrinthine ischemia and associated hearing loss by improving local cochlear health and local and systemic vascular endothelial health. This results from the advantageous modulation of intracellular $Ca^{2+}$ waves, the maintenance of vascular intraluminal fluidity by increasing cellular levels of NO (thereby augmenting the beneficial effects achieved by maintaining physiologic levels of vascular cGMP), by maintaining RBC deformability and by reducing the vascular risks associated with hyperinsulinemia secondary to reduced insulin sensitivity.

Because it maintains physiologic levels of NO and cGMP the invention improves general and local blood flow, increases reparative vascular endothelial cell proliferation, enhances inherent antithrombotic activities, reduces endothelial permeability, inhibits VSMC proliferation and inhibits cellular (neuronal and glial) apoptosis.

The systemic diseases most commonly associated with PSNHL are diabetes mellitus and hypertension—this is especially true when they coexist, as they often do. To the extent hyperinsulinemia and reduced insulin sensitivity exist in a significant portion of the general population, they also exist in the hearing loss population and are risk factors for hearing loss, notably although not exclusively, from changes in RBC rheology. By improving insulin sensitivity via (inter alia) insulin mimicry and voiding possibilities of hypomagnesemia, and concurrently reducing or preventing the clinical complications of hyperinsulinemia, the invention will reduce the vascular pathologies coexistent with labyrinthine ischemia and will aid in maintaining normal RBC deformability. In consequence, the invention will reduce the risks of sensorineural hearing loss associated with diabetes and hyperinsulinemia.

COMPONENTS OF THE INVENTION

Arginine

Dietary L-arginine improves NO-dependent vasodilatation and reduces vascular oxidative stress. L-Arginine exerts antihypertensive and antiproliferative effects on vascular smooth muscles, restores NO production and reduces the vascular release of superoxide anions. Endothelial dysfunction can be improved in both the coronary microvasculature and in epicardial coronary arteries by the administration of L-Arginine. Because an L-arginine-deficient diet reduces the hearing of treated animals a similar effect can be expected in the labyrinth vasculature. Indirectly inhibiting the production of NO by inhibiting eNOS increases the vulnerability of the myocardium to ischemia. Restoration of NO activity induces regression of preexisting intimal lesions providing evidence that long term L-arginine therapy can be clinically beneficial in lessening atherogenesis.

Absorption: Absorption of L-arginine is highest in the upper three gastrointestinal regions and least in the ileum. But no preferential site of absorption has been found.

Pharmacokinetics: The gastrointestinal uptake of dietary arginine when the stomach is in the "fed" state is about 20% to 38%.

Ascorbate

The outer cochlear hair cells transform sound into electrical signals, beginning the neural auditive process. In animal experiments antioxidants, including vitamin C, protective the outer hair cells of the cochlea.

The phase transfer rejuvenation of alpha tocopherol by ascorbate must occur to maintain and amplify D, alpha-tocopherol's chain-breaking effect on lipid peroxidation, the ultimate protection from free radical damage to cell membranes. (Synergism with alpha tocopherol is shared by two other components of this patent, ubiquinone and quercetin.) Ascorbate is also synergistic with taurine for $HOCl^-$ defense, with GSH or selenium for hydrogen peroxide defense and with SOD, zinc or copper for superoxide defense. (Superoxide and excess NO form peroxynitrite, an important tissue-damaging reactive species; GSH and ascorbate protect efficiently in this area, perhaps because ascorbate mimics stimulation of SOD activity by GSH.)

Ascorbate improves impaired acetylcholine-induced vasodilation by preventing oxygen free radical endothelial dysfunction and the associated reduction of constitutive NO.

Ascorbate is retained on the exterior cell surface of human erythrocytes, where it helps to protect the membrane from oxidant damage originating outside the cells. The ascorbate protects D, alpha-tocopherol in the erythrocyte cell membrane by a direct recycling mechanism.

Working together, ascorbate and D, alpha-tocopherol, maintain erythrocyte membrane integrity and deformability and preserve the antioxidant reserve of whole blood.

Absorption: Natural and synthetic ascorbates are avidly absorbed in the first 30 cm of jejunum.

Pharmacokinetics: As the daily oral dose vitamin C is increased, the concentration of ascorbic acid in the plasma and other body fluids does not increase proportionally, but approaches an upper limit. Analysis indicates that both saturable gastrointestinal absorption and nonlinear renal clearance act additively to produce a ceiling effect in plasma concentrations. As a consequence, there is no pharmacokinetic justification for the use of extremely large doses of vitamin C. Supplemental doses of ascorbate must be chosen carefully to avoid unwanted side effects. For example, recurrent renal stone formers or patients with renal failure who have a defect in vitamin C metabolism or patients with oxalate metabolism should restrict daily vitamin C intakes to approximately 100 mg.

Chromium

Chromium (Cr) reduces insulin resistance. Insulin resistance precedes almost all diabetes mellitus type 2, which accounts for 95% of all diabetes mellitus.

Hearing loss has long been associated with diabetes mellitus. Of all the metabolic, hormonal and vascular disorders considered to cause PSNHL, diabetes is the disease most commonly described. A hearing aid is three to four times more prevalent in patients with diabetes mellitus type 2 than in subjects without diabetes of the same age; not surprising, since about 50% of type 2 diabetic patients demonstrate impaired hearing.

Although Cr is an essential nutrient required for sugar and fat metabolism, routine dietary intake of Cr for humans is suboptimal. It has been proposed that 90% of American's diets are deficient in this essential trace element. Most diets contain less than 60% of the minimum suggested daily intake of 50 micrograms. Insufficient dietary intake of Cr leads to signs and symptoms that are similar to those observed for diabetes. Supplemental Cr given to people with impaired glucose tolerance or with overt diabetes improves blood glucose, insulin, and lipid variables. Any response to Cr, however, is dependent upon the form and amount of supplemental Cr. For example, trivalent Cr ($Cr^{+3}$) has a very large safety range and there have been no documented signs of toxicity in any of the $Cr^{+3}$ nutritional studies up to levels of 1 mg per day.

Absorption: Even with significant dietary Cr intakes, only a small fraction of the ingested Cr, is absorbed; most, congruent with intake, is excreted in the stool. Urinary Cr is constant from day to day. The Cr balances (apparent net retention) remain in positive equilibrium. In one small study, the average apparent net absorption of Cr was 1.8%.

Pharmacokinetics: Principal Cr concentrations are found in the liver, spleen, soft tissue, and bone. Most dietary nutrients and metabolites do not alter Cr retention or distribution. The regulation of Cr homeostasis appears to be modulated by excretion.

CoQ10

Coenzyme Q10 (CoQ10) has already favorably been evaluated in the clinical treatment of heart disease. In the otolaryngological field, it has been reported that CoQ 10 is effective in promoting recovery from acute, sudden deafness. The pharmacokinetics of CoQ10 in the inner ear indicate that CoQ10 is effective in promoting recovery of damaged auditory hair cells by preventing respiratory metabolic impairment of these cells due to hypoxia. In CoQ10 treated animals, the chronic depression of hearing is milder than that in the control animals.

In addition to assisting ascorbate in the phase transfer rejuvenation of D, alpha-tocopherol, CoQ10 further complements alpha tocopherol by directly inhibiting lipid peroxidation. As one example: low-density lipid 3 (LDL3)-bearing serum, the densest of the three LDL subfractions, shows statistically significant lower levels of CoQ10. This condition is associated with elevated hydroperoxide levels when compared with the lighter counterparts. After CoQ10 supplementation, LDL3 responds with a significant decrease in the hydroperoxide level. These results support an hypothesis that raising CoQ 10 endowment in subfractions of LDL lessens their oxidizability.

Absorption: Supplemental oil-based capsules of CoQ10 elevate CoQ10 in plasma by 178% while granular preparations increase COQ10 in plasma by 168%. Each form is therefore an acceptable delivery vehicle.

Pharmacokinetics: After oral administration of 100 mg of d5-CoQ10 to sixteen healthy male subjects, the mean plasma CoQ10 level attained a peak of 1.004+/−0.37 micrograms/ml within 6.5 to 8 hours after administration and the terminal elimination half-life was 33 to 38 hours. In most of the subjects, plasma d5-CoQ10 showed a second peak 24 h after dosing. This unusual plasma level curve can be explained by a 'compartment' model in which absorbed CoQ 10 is taken up by the liver, transferred mainly to very low-density lipids (VLDL) and distributed to the systemic blood.

Folate

Age-related auditory dysfunction may be associated with poor vitamin B- 12 and folate status.

In 1992–93, an epidemic outbreak of peripheral neuropathy (50,862 cases; (incidence rate: 461.4 per 100,000) affected Cuba. Clinical forms included retrobulbar optic neuropathy, sensory and dysautonomic peripheral neuropathy, dorsolateral myeloneuropathy, sensorineural deafness, dysphonia and dysphagia, spastic paraparesis, and mixed forms. Deafness produced selective high frequency (4–8 kHz) hearing loss. Intensive searches for neurotoxic agents—in particular organophosphorus esters, chronic cyanide and trichloroethylene intoxication—were negative. However, treatment of patients with B-group vitamins and folate produced rewarding results. Supplementation of multivitamins to the entire Cuban population curbed the epidemic. Overt malnutrition was not present but a deficit of micronutrients, in particular thiamine, cobalamine, folate and sulfur amino acids appears to have been a primary determinant of this epidemic.

Homocysteine is an independent risk factor for cardiovascular disease. Hyperhomocysteinemia is associated with arteriosclerosis, atherosclerosis, decreased GSHPx activity, vasoconstriction, endothelial toxicity and thromboembolic events and the prevalence of arterial occlusive disease is high mild in young patients with hyperhomocysteinemia. In about 90% of such patients, treatment with vitamin B6 plus folic acid normalizes the homocysteine concentration. Reducing homocysteine-induced endothelial dysfunction complements the anti-vasoconstrictive and anti-thrombogenic components of this invention. The three key biofactors that favorably alter homocysteine metabolism are included in the invention: folic acid, pyridoxine and cyanocobalamin ($B_{12}$).

Folic acid stimulates BH4 regeneration. This is an essential cofactor required for the conversion of L-arginine to NO under the influence of Type III NOS (constitutive endothelial eNOS) within the endothelial cell membrane (see details above). Additionally, folic acid reduces the catabolism of NO and improves the bioavailability of endothelial-derived NO.

Absorption: Folic acid is absorbed in the first 30 cm of the jejunum by both saturable and diffusional routes.

Pharmacokinetics: Folic acid is a coenzyme which humans, unlike bacteria, cannot synthesize de novo; therefore it is a dietary essential. Folic acid is converted to the active coenzyme tetrahydrofolate (THF) by repeated hydrogenation of the pterin ring. The coenzyme THF is then capable of one-carbon-residues transfers of different oxidation states.

Gingko Biloba

The main mechanisms of action of Ginkgo biloba are vasoregulation (increased blood flow), platelet activating factor antagonism and prevention of membrane damage caused by free radicals, all activities that reduce tissue ischemia. Since ischemia is one pathogenic mechanism behind acute cochlear deafness, it is understandable that Ginkgo biloba significantly improves recovery from acute cochlear deafness and that used in animals it reduces sound damage from white noise or from a pure tone at 4.5 kHz.

Hearing loss secondary to hematologic factors may be lessened by Ginkgo biloba supplementation. In a prospective study, twenty patients with a long history of elevated fibrinogen levels and plasma viscosity were treated with the Ginkgo biloba extract, EGb 761 (240 mg tablets a day for a period of 12 weeks). Fibrinogen levels and hemorrheological properties significantly improved.

Controlled clinical trials have been evaluated in a meta-analysis to evaluate the effectiveness of Ginkgo biloba on symptoms of cerebrovascular insufficiency in old age. All the included studies were placebo-controlled, randomized, double blind studies using a daily dosage of 150 mg ginkgo biloba. Seven of eight studies confirmed the effectiveness of Ginkgo biloba compared to a placebo, while only one was inconclusive.

Absorption: The absorption of EGB is about 60%. Different formulations of Ginkgo biloba extracts (e.g., capsules, drops or tablets) appear to be bioequivalent.

Pharmacokinetics: The ginkgolides and bilobalides, which are compounds extracted from the dried leaves of the Ginkgo biloba tree, have high bioavailability when given orally during fasting. The bioavailability coefficients (FAUC) have mean values equal to 0.80 (+/−0.09), 0.88(+/−0.21) and 0.79(+/−0.3) for Ginkgolide A, Ginkgolide B and Bilobalide respectively. Food intake does not change FAUC quantitatively but increases Tmax.

Glutathione and Glutathione Prodrugs

A principal mechanism of hearing loss due to acoustic over stimulation is reactive ROS generation and ROS not removed by antioxidant defenses cause significant damage to the sensory cells of the cochlea. GSH inhibition increases the susceptibility of the cochlea to noise-induced damage. Replenishing GSH, by enhancing availability of cysteine, attenuates noise-induced cochlear damage. As an example, the GSH prodrug OTC promotes rapid restoration of GSH when GSH is acutely depleted. GSH synthesis is markedly upregulated selectively in the lateral cochlear wall by noise exposure in response to the consumption of GSH as the latter is utilized in scavenging ROS. This emphasizes the importance of adequate supply of GSH and supports supplementation of GSH prodrugs for the prevention and treatment of noise-induced hearing loss (NIHL). Depletion of endogenous GSH potentiates NIHL, whereas replenishment of GSH attenuates NIHL.

The body possesses complex protective antioxidant systems against ROS production, such as dismutase superoxides, catalases, metallic ion sequestration, enzymes which degrade proteins damaged by ROS, metabolizing hydroperoxides, DNA repair processes, vitamins E, C and, in particular, the GSH enzyme system. A physiological steady state is established under normal conditions between the production of oxidants and their neutralization by antioxidants.

GSH levels cannot be raised predictably by supplemental administration in the diet. Because of peptidase activity in the small intestine most peptides undergo rapid degradation in the lumen of the gastrointestinal tract. There is evidence that limited uptake of small (dipeptides and tripeptides) is possible. But the bioavailability of orally administered peptides generally is low. Aside from this, even if absorption from the gastrointestinal tract is sufficient to raise plasma levels, questions remain regarding their ability to gain passage into cells.

Concern that raising plasma levels of GSH could stimulate a negative feedback loop down regulating intracellular GSH production should be addressed. Therefore, until these issues are resolved it is probably best to administer GSH precursors.

Reduced GSH is important and ubiquitous. It is necessary for intracellular transduction signaling, for the modulation of cellular apoptosis and necrosis, and the modulation of red blood cell fragility. During its function as an antioxidant it is oxidized to disulfide glutathione (GSSG). This oxidation importantly protects vascular endothelium from free radical damage. GSH inhibits the peroxidation of LDL directly reducing atherosclerotic and vasoconstrictive risks, and oxLDL-induced mitochondrial DNA mutations. Besides their influence upon atherogenesis and vasoconstriction, these effects are linked to a variety of specific sensory neuropathies.

GSH plays multiple roles in the nervous system including free radical scavenging, redox modulation of inotropic receptor activity and neurotransmission. GSH depletion enhances oxidative stress and increases the level of neuroexcitotoxic molecules; in distinct neuronal populations including the auditory system, both of these events can initiate cell death.

Exposure to glutamate, an important neurotransmitter, causes depletion of intracellular mitochondrial GSH leading to the accumulation of ROS and, ultimately, apoptotic cell death. Cells which have enhanced rates of GSH regeneration due to higher activities of the GSH metabolic enzymes gamma-glutamyl cysteine synthetase and GSH reductase appear to be resistant to glutamate-induced ROS. Not surprisingly, maintenance of intercellular GSH level appears to exert a neuroprotective effect.

Because the protection of the electron acceptor homocysteine thiolactone declines with aging, homocysteine levels frequently increase. GSH levels are lowered by homocysteine.

GSH is low in the presence of hypomagnesemia. Hypomagnesemia is commonly present in the aging (and the diabetic) population.

Redox-sensitive mechanisms are involved in VSMC growth with attendant ischemia and apoptosis. ROS that promote VSMC growth are inhibited by GSH. This might be expected since upon oxidation micronutrients need to be regenerated in the biological setting, hence their need for coupling to nonradical reducing systems such as GSH/GSSH or NADPH/NADP+ and NADH/NAD+.

Cysteine is a necessary thiol precursor of GSH. GSH predecessors (NAC, 2-OTC, MPG) supply cysteine residues to cells for GSH synthesis. These prodrugs, which do in fact increase GSH levels, protect endothelial cells from atherosclerotic damage, perturbations of laminar flow, VSMC hypertrophy, cell detachment, etc., help to preserve a normal NO/ET-1 ratio and protect against NIHL.

Absorption: NAC is one example of a precursor of GSH used in this invention. Intestinal absorption of NAC is satisfactory. After an oral dose of 200 to 400 mg of NAC, peak plasma concentration is achieved within 1 to 2 hours. The upper jejunum is a principal site of some, but very limited, GSH absorption. This low GSH bioavailability is not increased by higher doses. Orally administered GSH at reasonable levels does not affect the circulating concentrations of GSH, whereas NAC administration increases the GSH content in lungs, blood and/or liver.

Pharmacokinetics: The administration of NAC increases hepatic cysteine placing it on a path for the modulation of systemic GSH levels. Following supplementation, pharmacokinetic and pharmacodynamic studies of NAC demonstrate elevated GSH levels in plasma, RBC and peripheral blood lymphocytes (PBL), elevated cysteine levels in plasma and increases in two, GSH-metabolizing enzymes, glutathione S-transferse and oxidized glutathione reductase, in the PBLs. These studies have established NAC as the precursor of GSH.

alpha-Lipoic Acid

Dose-dependent otoprotection in animals is conferred by lipoate by sparing of the cochlear antioxidant defense system. The proglutathione metabolic antioxidant alpha-lipoic acid (LA) (1, 2-dithiolane-3-pentanoic acid) is a low molecular weight substance that is absorbed from the diet, is both water- and lipid-soluble and crosses the blood-brain barrier. Within cells and tissues the salt form (alpha-lipoate) is reduced to an even more active structure, dihydrolipoate, which is exported to the extracellular medium; hence, antioxidant protection is afforded to both the oxidized and reduced forms, within both intracellular and extracellular environments. LA acts as a mitochondrial coenzyme that is involved in reversing declines in cellular $O_2$ consumption and impaired mitochondrial membrane potentials. It is important in decreasing malondialdehyde (MDA) levels (an indicator of lipid peroxidation), in regenerating ascorbic acid and increasing GSH levels in rats.

Since alpha-lipoate and dihydrolipoate forms have been shown to be potent antioxidants, both the oxidized and reduced forms of LA have antioxidant activity and either form can regenerate through redox cycling other antioxidants like ascorbic acid and alpha-tocopherol, and raise intracellular GSH levels. LA can be directly administered as a dietary supplement, whereas GSH cannot. These various features make it evident that LA may be useful in reducing the twin conditions of vasoconstriction and ischemia associated with acute or chronic cochlear damage.

After oxidative stress induced by hypoxia/reoxygenation and treatment with LA, there is distinct improvement of mitochondrial structure/function. Loss of GSH accompanied by concurrent mitochondrial dysfunction, can be inferred in vitro by losses of Complex I activity in male mouse brain slices and in vivo in selected regions of mouse CNS exposed to excitatory amino acids. The inhibition of Complex I is abolished by the maintenance of protein thiol homeostasis with pretreatment with GSH or with LA.

Transcription factor NF-kappaB is a cell-signaling pathway. It leads, for example, to gene expression in keratinocytes after exposure to solar UV radiation (UVR). Exogenous supplementation of antioxidants prevents UVR-induced photo-oxidative damage. While high concentrations of NAC can inhibit NF-kappaB activation, low concentrations of LA have a similar significant effect. These results indicate that the very efficient antioxidant properties of LA may lay in their selective action on NF-kappaB activation.

Reduced GSH is a cofactor for the glyoxalase system, a metabolic pathway that catalyses the detoxification of alpha-oxoaldehydes (RCOCHO) to corresponding aldonic acids (RCH(OH)CO$_2$H). The glyoxalase system protects cells from alpha-oxoaldehyde mediated formation of advanced glycation end products (AGE). AGE's are implicated in a wide variety of diabetic vascular abnormalities and, perhaps, in the pathogenesis of age related processes such as hearing loss and macular degeneration. Studies have found that incubation of cultured bovine aortic endothelial cells (BAECs) with AGE albumin results in decreases of GSH and ascorbic acid levels. This increased cellular oxidative stress leads to the activation of NF-kappaB and promotes the upregulation of various NF-kappaB-controlled genes, including endothelial tissue factor. However, the addition of LA before AGE exposure completely prevents depletion of GSH and ascorbic acid by inhibiting the release and translocation of NF- kappaB from the endothelial cytoplasm into the nucleus. Because LA reduces this AGE-induced NF-kappaB mediated transcription, the expression of endothelial genes such as tissue factor and the vasoconstrictor ET-1 is reduced.

Redox-sensitive mechanisms are involved in VSMC growth. ROS that promote VSMC growth are inhibited by GSH and also are negatively influenced by LA. In addition to lessening VSMC hypertrophy, supplemental thiols such as LA that increase GSH levels, protect endothelial cells from damage. This helps preserve a normal NO/ET-1 ratio and limit perturbations of laminar flow, thereby reducing the probability of the phase shift in blood flow associated with NIHL. By providing additional improvement in GSH synthesis and thus augmenting intracellular GSH, LA also improves NO-dependent, flow-mediated dilation.

Absorption: Non-saturable kinetics of LA in healthy volunteers is demonstrable from single oral doses in the range of 200 to 600 mg. Thioctic acid is a rapidly absorbed, racemate of R-(+)- and S-(−)-enantiomers of LA which acts as a powerful lipophilic, free radical scavenger. Oral LA supplementation in rats increases levels of free LA in the gastrocnemius muscle and increases total GSH levels in the liver and blood.

Pharmacokinetics: In one study, the absolute bioavailability of LA in humans after a 200 mg oral dose was 29.1+/−10.3%. In rats given oral doses of ($C_{14}$) LA, the area of ($C_{14}$) LA in the plasma concentration-time curve (FAUC) was 66% of that following similar intravenous administration.

Magnesium

In animal experiments, correlations were observed between serum $Mg^{2+}$ levels and noise-induced permanent hearing threshold shifts (NIPTS); dietary supplementation with $Mg^{2+}$ has been shown to reduce hearing loss in noise-exposed rats. Encouraged by this, the prophylactic effect of $Mg^{2+}$ in humans exposed to noise was investigated. The subjects were 300 young, healthy, and normal-hearing recruits who underwent 2 months of basic military training. This training necessarily included repeated exposures to high levels of impulse noises while using earplugs. During this placebo-controlled, double blind study, each subject received daily 167 mg of elemental $Mg^{2+}$ or placebo. NIPTS were significantly more frequent and more severe in the placebo group than in the $Mg^+$ group. NIPTS were negatively correlated to the $Mg^{2+}$ content of blood red cells and mononuclear cells. This study demonstrated the effectiveness of oral $Mg^{2+}$ supplementation in reducing hearing damage from conditions of high level, impulse noise exposure.

Cell membrane permeability is increased in hypomagnesemia, causing $Na^+$ and $Ca^{2+}$ influx and subsequent increased demands in energy-dependent, ion pumping. At the same time energy depletion in the hair cells appears to be one cause of noise-induced hearing loss, this energy exhaustion may be worsened by hypomagnesemia-induced vasoconstriction.

As discussed earlier, $Ca^{2+}$ in cochlear hair cells controls mechanical transduction, triggers neurotransmitter release and mediates efferent synaptic signaling. These activities are modulated by a $Mg^{2+}$-dependent outward current governed by the activity of plasma membrane $Ca^+$-ATPase (PMCA). As a result the concentration of intracellular $Ca^{2+}$ is reduced and noise signaling is moderated.

The concentration of free $Mg^{2+}$ is important in the type of vascular disease that is associated with the hearing loss of aging. Effects on smooth muscle tone, serum lipid and lipoprotein levels, free radical production and energy metabolism are all linked to $Mg^{2+}$ concentration. Until recently it was not realized that $Mg^{2+}$ played such an important role in vascular dynamics. This lack of understanding, in part, reflects a poor appreciation of the progressive shortfalls in dietary $Mg^{2+}$ intake since the early 1900s and a failure to recognize that patients whose diets are deficient in this element are not necessarily hypomagnesemic. At the turn of the century average dietary intake of $Mg^{2+}$ in the USA was about 450 to 485 mg per day, which is accepted as a reasonable daily consumption to meet the requirements of cellular metabolism. The most recent figures indicate that a typical daily intake is now about one-half of this, so that there is now a typical dietary magnesium shortfall of 90 to 180 mg per day in this country.

The level of $Mg^{2+}$ is an important determinant of vascular tone, contractility and reactivity. By a variety of mechanisms, $Mg^{+2}$ functions both intracellularly and extracellularly to optimize the cytoplasmic free $Ca^{+2}$ level. Although the latter element is a critically important intracellular messenger, excessive cytoplasmic free $Ca^{+2}$ causes an increase in ET-1, with an associated decrease in blood flow, platelet aggregation and cell apoptosis. The correction of a $Mg^{+2}$ deficiency prevents or reverses the hypertensive, thrombotic and atherosclerotic effects of overabundant intracellular $Ca^{+2}$. $Mg^{+2}$ accomplishes this without interfering with normal $Ca^{+2}$ intracellular signaling. Clinically prescribed pharmaceutical calcium channel blockers (e.g., nifedipine) have amplitude-driven effects on $Ca^{+2}$ cellular signaling, which can be deleterious and occasionally fatal. Physiologic modulation of cell signaling requires a fine balance involving $Ca^{+2}$ flow patterns between the cell membrane, the plasma and the endoplasmic reticular substances, and $Ca^{+2}$ flow patterns within and from the cytoplasm. In addition to facilitating the ATPase energy requirements for modulation of $Ca^{+2}$ signaling, $Mg^{+2}$ exerts important regulatory effects on the precise subcellular location and concentration of both $Ca^{+2}$ and $Mg^{+2}$ Absorption: $Mg^{2+}$ is absorbed by active transport in the ileum although there is limited passive diffusion throughout the intestine.

Pharmacokinetics: There is a maximum intestinal bulk absorption of $Mg^{2+}$ of 8 mEq per meal with a curvilinear falloff and $Mg^{+2}$ absorption is negatively influenced by dietary protein: e.g., soybean protein, when compared with casein, decreases $Mg^{+2}$ absorption through its phytate component. Both this bulk absorption ceiling and the dietary protein influences speak to the importance of supplementing $Mg^{+2}$ in multiple doses per day.

Melatonin

Melatonin, which is normally present in cochlear cells, has been shown to have a protective role on the postmortem activity of the outer cochlear hair cells of the rat, prolonging hair cell activity after death up to 7 times compared to untreated animals.

Melatonin, N-acetyl-5-methoxytryptamine, is a hormonal product of the pineal gland which is highly lipophilic and readily enters all cells and tissues in the body, including the brain. In addition to stimulating mRNA for both GSHPx and superoxide dismutase it is, itself, a very potent hydroxyl and peroxyl radical scavenger. It is suggested that as an intracellular free radical scavenger it is at least equal to GSH and vitamin E, affording protection to molecules (especially DNA) from oxidative damage. Melatonin's extremely high diffusibility is important for its scavenging action because this feature allows it to enter all cells and every subcellular compartment, including the nucleus. Melatonin is one of the premier molecules to protect the organism from oxidative damage.

Within 30 minutes exogenously administered melatonin causes a 2-fold rise in GSHPx activity in the brain. Brain GSHPx activity is higher at night than during the day and is correlated with high nighttime tissue melatonin levels. GSHPx is thought to be the principal enzyme for eliminating peroxides in the brain. It reduces the formation of hydroxyl radicals (formed via iron-catalyzed, Fenton-type reactions from hydrogen peroxide) by reducing this oxidant to water. Since the hydroxyl radical is the most noxious oxygen radical known, induction of brain GSHPx may be an important mechanism by which melatonin exerts its potent neuroprotective effects. In addition to increasing levels for GSHPx melatonin increases mRNA for superoxide dismutase, another important cellular antioxidant enzyme. These mRNA stimulatory effects are observed after both acute and chronic melatonin treatment.

Absorption: Ingestion of 3 mg melatonin causes a marked increase in serum melatonin (3561+/−1201 pG/mL) within 20 min. Although this is followed by a gradual decrease, the level still remains higher than the basal level at 240 min after ingestion.

Pharmacokinetics: When huge doses of melatonin (80 mg) are administered orally, changes in serum melatonin levels are best described by a biexponential equation with an absorption constant (ka) of 1.72 h-1 (half-life=0.40 h) and an elimination constant kel) of 0.87 h-1 (half-life=0.80 h). Peak serum melatonin occurs 60–150 min after its administration, remaining stable for approximately 1.5 hours.

Nicotinamide

Improvements of rheological properties of blood and red cell deformability by alpha tocopherol nicotinate (TN) occur and are thought to be due mainly to reduced lipid peroxidation stress on the membrane of red blood cells. Whether the effect might also relate to the availability of nicotinamide (NAD) and nicotinate as an NAD precursor is reasonable, but has not yet been investigated. Alpha-tocopherol nicotinate 300 mg tid, after meals, for 3 months in Type 2 diabetes mellitus resulted in significant reductions of blood viscosity at different shear rates (e.g. −2.23 +/−2.82 p0.015, gamma= 1.5 s(−1)) and viscoelasticity (p0.004); resistance of erythrocyte deformation (p0.001) and lipid peroxidation stress in red cell membrane (malondialdehyde or MDA reduced by 0.17+/−0.13 nmol l(−1) p0.005).

The water-soluble vitamin NAD, or niacin, has established itself as a useful oral supplement for patients who require reduction of plasma oxLDL, a decrease in plasma fibrinogen levels and stimulation of fibrinolysis. Such supplementation decreases plasma fibrinogen and low-density lipoprotein cholesterol in subjects with peripheral vascular disease and can cause a significant elevation in liver NAD+, serving to ensure the continuous NADPH production via the pentose pathway which is important in maintaining protective levels of GSH. Additionally, recent findings suggest that the NAD+ precursors nicotinic acid and nicotinamide protect against oxidative stress and DNA damage by up-regulating the stress response genes GAPDH and G6PD.

The inhibitory effect of TN upon hydrogen peroxide-induced platelet aggregation has been found to be greater than that of either vitamin E alone or the simultaneous use of vitamin E and nicotinic acid. Nicotinic acid alone showed no inhibitory effect. It is suggested that the effect of TN is not due to any additive effects of vitamin E and nicotinic acid produced by hydrolysis, but to the unique and distinctive property of this molecule itself. Because of this unique property, TN is the molecular form of nicotinic acid most commonly used in products relating to this patent. The alpha tocopherol moiety of TN is taken up by red blood cell membranes and the nicotinate moiety is distributed among red blood cell contents. The main metabolite in both red blood cell contents and liver after a single orally administered dose of TN is nicotinamide.

Absorption: Immediate release dosage forms of nicotinamide achieve higher plasma levels than sustained release. Formulations at high doses produce nonlinear kinetics, e.g., a 10-fold increase in the dose of standard nicotinamide produces a 62-fold increase in the AUC.

Pharmacokinetics: Nicotinamide is a derivative of the B vitamin niacin. There appears to be no significant difference in the kinetics of low dose standard nicotinamide (2.5 mg/kg) and low-dose, long acting nicotinamide (Enduramide®) (6.7 mg/kg). Nonlinear kinetics is found with both formulations at higher doses. The FAUC is significantly greater with the standard formulation, indicating a higher bioavailability. The AUC for standard nicotinamide is 1.7 times higher than that for Enduramide®.

Riboflavin

Erythrocytes lack mitochondria and other organelles and thus their cytoplasmic metabolism is much reduced. A small portion of the glucose transported into RBCs is metabolized via the glucose hexose-monophosphate pathway. The NADPH thus formed is important for processes involved in protecting RBCs from ROS. In addition to damaging intracellular molecules, cellular organelles and membranes, ROS convert hemoglobin into inactive methemoglobin.

Selenium-containing GSHPx converts peroxide groups into harmless hydroxyl units utilizing GSH as its substrate. The thiol group of the cysteine moiety is oxidized to the disulfide during the reduction of methemoglobin and peroxides. The regeneration of GSH is catalyzed by glutathione reductase, which in turn, uses NADPH as the reducing agent. The latter function is dependent on riboflavin.

The GSH content and glutathione reductase activity in the liver are decreased by deficiencies of riboflavin. However the riboflavin GSH content and activity of glutathione reductase returns to the control level of riboflavin-supplemented rats in 24 h and the lipid peroxide level recovers in 48 h. These findings indicate that increases of lipid peroxide in the livers of riboflavin-deficient rats is caused by the decrease in the GSH content as well as glutathione reductase activity rather than by decreases in the selenium-dependent GSHPx activity.

If the recommended daily of riboflavin intake is 0.5 mg/l 000 kcal (as is true), 23% of males and 7% of females are deficient in dietary riboflavin.

Absorption: Saturable (active transport) and nonsaturable (energy-independent) diffusion of riboflavin occur throughout the rat small intestine.

Pharmacokinetics: A small circadian variation in riboflavin levels occurs; plasma concentrations and urinary excretion of riboflavin are lowest during the afternoon. Since riboflavin has the potential to increase gastrointestinal iron absorption in the stomach, it is included in the delayed release portion of the combination dosage form of the invention to avoid this result.

Selenium

Given the defined importance of the GSH/GSHPx system in preventing and treating NIHL, the necessity of adequate selenium (a GSHPx cofactor) is self-evident.

Selenium treatment results in a significant elevation of RBC GSHPx an increase in glutathione reductase activities and in GSH content by 64%, 57%, and 11%, respectively; this effect is also paralleled by a 39% reduction in the RBC oxidized GSH content. On termination of selenium treatment and after 3 months on placebo, all of these elements of the GSH system return toward baseline levels. Dietary selenium activates the GSH system and is thereby a potent antioxidant cofactor against plasma and LDL lipid peroxidation.

In mice, selenium supplementation increases GSH content and GSHPx activity in peritoneal macrophages by 36% and 30% respectively and this effect is associated with a 46% reduction in cell-mediated oxidation of LDL and aortic atherosclerotic lesions. These data demonstrate an inverse relationship between macrophage GSH content/GSHPx activity and cell-mediated oxidation of LDL and imply that enhancement of the macrophage GSH/GSHPx system contributes to attenuation of the atherosclerotic process.

Absorption: Sodium selenite is absorbed slowly, possibly by simple diffusion through the intestinal mucosa.

Pharmacokinetics: Thiols positively influence mucosal uptake of selenium. As an example, L-cysteine stimulates selenium uptake in the middle and distal jejunum and cecum, but not in the proximal jejunum. This effect is maximal in the distal jejunum. The absorption of amino acid-bound selenium is accelerated by specific amino acid active transport mechanisms in the gut mucosa.

Taurine

We have established that $Ca^{+2}$ is a critically important intracellular messenger and that its intracellular signaling, occurring infrequency modulated waves, can be modified by calcium channel blockers which change the amplitude of $Ca^{+2}$ entering the cell. This modulated signaling requires an enzyme-controlled fine balance between the plasma and the endoplasmic reticular substances and $Ca^{+2}$ flow patterns within and from the cytoplasm. As described above, $Mg^{+2}$ is a key cofactor. Similarly, the amino acid taurine improves cellular $Ca^{+2}$ dynamics and is functionally complementary to $Mg^{+2}$.

Taurine is an amino acid, which is not utilized in protein synthesis, but rather is found free in the cytoplasm or in simple peptides. It is important for the modulation of cellular $Ca^{+2}$ levels, cell membrane stabilization and osmoregulation, and has been used with some success in the treatment of neurodegenerative diseases, including macular degeneration and Alzheimer's disease. There is consistent evidence from other studies that taurine reduces toxic effects on neurons. While taurine increases cytosolic $Ca^{+2}$ transients in cardiac cells (and thus has positive inotropic activity), in other cells it tends to reduce cytosolic $Ca+^2$ consistent with its role as a modulator of $Ca^{+2}$ intracellular signaling. Similar to $Mg^{+2}$, taurine lowers elevated blood pressure, retards cholesterol-induced atherogenesis, prevents arrhythmias, and stabilizes platelets and cell membranes. Its favorable modulation of $Ca^{+2}$ signaling complements the similar action of $Mg^{+2}$ and its stabilization of cell membranes augments other components of this invention.

Absorption: Taurine uptake across the intestinal brush border membrane of the adult cat seems not to require a specific transport mechanism, although the steady-state uptake of taurine by rat intestinal cells is saturable.

Pharmacokinetics: Even at a low concentration taurine seems to enhance drug absorption—especially lipid soluble drugs—due to its effect on the permeability characteristics of the mucosal membrane. Bile salts are synthesized in the liver from cholesterol conjugated with taurine. Within the gastrointestinal lumen these bile salts play an essential role in lipid absorption and fat transport.

alpha-Tocopherol (See extended comments above regarding rheology.)

Improvements of Theological properties of blood and red cell deformability by alpha-tocopherol occur and are mainly attributed to reducing lipid peroxidation of red blood cell membranes. 300 mg tid of alpha-tocopherol taken after meals for 3 months results in significant reductions of blood viscosity at different shear rates and viscoelasticity. The resistance of erythrocyte deformation and lipid peroxidation stress in red cell membrane (malondialdehyde or MDA) is reduced by 0.17+/−0.13 nmol.

Fibronectin is significantly increased in patients with sensorineural hearing impairment, suggesting that microvascular endothelial damage is a factor in these patients. D, alpha-tocopherol is generally regarded as the most important lipid-soluble, chain-breaking antioxidant in maintaining the integrity of the vascular endothelial cells plasma The lipid soluble, free oxygen radical scavenger, D, alpha-tocopherol has a variety of antioxidant activities which include among others: promotion of the Ach/cAMP synthesis of NO, decomposition of fatty acid hydroperoxides and hydrogen peroxides, maintenance of cell membrane stability, maintenance of RBC deformability, reduction of blood viscosity and viscoelasticity; prevention of DNA strand breakage, improvement in the uptake of glutamate by synaptosomes at neural junctions and the suppression of oxidation of oxLDL.

The antioxidant defense of elderly patients is improved with low doses of supplemental vitamin E, and following supplementation with D, alpha-tocopherol GSHPx activities increase as much as twofold. The importance of maintenance of GSH in reducing noise induced hearing loss has been addressed previously, as was its prevalence in the elderly.

Studies of the effectiveness of D, alpha-tocopherol in preventing or treating human pathology utilize dosages of 200 to 800 mg daily, which exceed amounts that can be obtained from an average diet and the current recommended daily allowance for healthy people. Thus supplementation at these levels is appropriate in therapeutics and disease prophylaxis.

Absorption: The gastrointestinal absorption of dietary D, alpha-tocopherol is dependent upon the simultaneous digestion and absorption of the fat in which the vitamin is solubilized. Taurine may enhance D, alpha-tocopherol absorption. The site of D, alpha-tocopherol absorption is probably the proximal small intestine.

Pharmacokinetics: Evidence suggests that further uptake of the tocopherols occurs in the deep cryptal zone of the colonic mucosa where actively proliferating cells extract nutrients from the systemic circulation.

Vanadium

Vanadium reduces insulin resistance. Insulin resistance precedes almost all Type 2 diabetes, which accounts for 95% of all diabetes mellitus.

Hearing loss is associated with diabetes mellitus. It is the most common causative metabolic disorder related to PSNHL. A hearing aid is three to four times more prevalent in patients with diabetes mellitus type 2 than in subjects without diabetes of the same age and about one-half of type 2 diabetic patients have impaired hearing.

The pathophysiologic importance of insulin resistance in diabetes mellitus has been established. Complexes of vanadium mimic the metabolic actions of insulin in improving glycemic control in humans with diabetes. In addition to its direct insulin mimetic actions, vanadium salts also modulate insulin metabolic effects by enhancing insulin sensitivity and prolonging insulin action. All of these actions appear to be related to protein tyrosine phosphatase (PTP) inhibition. The precise biochemical vanadate pathways of action are not yet known, but they are different from insulin in that the receptor for insulin and the enzyme phosphatidylinositol 3'-kinase do not seem to be essential for vanadate stimulation of glucose uptake and metabolism.

Vanadium can 'bypass' defects in insulin action in diseases characterized by insulin resistance. Vanadium salts also have an apparently preferential metabolic (versus mitogenic) signaling profile. These characteristics make vanadium compounds exciting pharmacological agents to reduce insulin resistance and improve diabetes associated hearing loss.

Vitamin A (beta-Carotene)

Vitamin A is found in the guinea pig cochlea at a concentration ten times that found in most other tissues. The effect of vitamin A deficiency in guinea pigs on noise-induced temporary threshold shift (TTS) was evaluated after short (15 min) acoustic over stimulation with a moderate (90 dB) broad-band white noise. Guinea pigs were fed, ad libitum, a purified diet deficient in vitamin A until biochemical signs of deficiency occurred. This resulted in caused a reduction in N1-amplitude and N1-latency in the vitamin A deficient, sound-stressed group; presumably this reflected changes in inner ear hair cell activity. The authors concluded that vitamin A deficiency increases the sensitivity of the inner ear to noise and that this increased sensitivity raises the probability of noise-induced hearing loss. In another study, after feeding young rats a diet deficient in vitamin A there were changes in the outer and inner hair cells and massive degenerative changes in the ganglion cells of the VIII nerve. In humans suffering from alcoholic liver disease there is decreased auditory function associated with low vitamin A levels. Studies also have shown some improvement in presbycusis in patients treated with vitamins A (and E) for 28–48 days.

Vitamin B6 (Pyridoxine)

Pyridoxine complements folic acid in reducing plasma homocysteine. Inducible iNOS (a Type II gene product)

within activated macrophages contributes to the inflammation that characterizes early atherogenesis and may, in part, account for the adverse vascular effects of hyperhomocysteinemia. Evidence suggests that the expression of iNOS in VSMCs may, in part, promote atherosclerosis by increasing local oxidative stress caused by high (toxic) local levels of NO. However, within activated macrophages the incorporation of pyridoxine (and of folic acid) lessens the conversion of L-arginine to toxic levels of homocysteine-induced NO from iNOS Type II. This adds an element of safety to the invention.

Absorption: Pyridoxine absorption in the jejunum (rat) is nonsaturable and consistent with passive diffusion. The gastrointestinal concentrations of pyridoxine in various intestinal segments tend to parallel those of riboflavin, suggesting some similarity of absorption characteristics. While the gastrointestinal absorption characteristics may be similar to riboflavin, it is unclear if it also enhances iron absorption like the latter.

Pharmacokinetics: Studies have suggested that a physiological dose of pyridoxine is transformed to pyridoxal in the intestinal tissues and then released in this putatively active form into the portal blood.

Vitamin $B^{12}$ (Cyanocobalamin)

There is convincing evidence that poor vitamin $B^{12}$ and folate status is associated with age-related auditory dysfunction. A thorough audiometric assessment was conducted in 55 healthy women aged 60–71 yrs. Hearing function was determined by the average of pure-tone air conduction thresholds at 0.5, 1, 2, and 4 kHz and was categorized into 2 groups for logistic regression analyses. The mean age was the same (65 y) for the normal and the impaired hearing groups. Pure-tone averages were inversely correlated with serum vitamin $B^{12}$ ($r=-0.58$, $P=0.0001$) and red cell folate ($r=-0.37$, $P=0.01$). Women with impaired hearing had 38% lower serum vitamin $B^{12}$ and 31% lower red cell folate than women with normal hearing. Among participants who did not take supplements containing vitamin $B^{12}$ or folate, women with impaired hearing had 48% lower serum vitamin $B^{12}$ and 43% lower red cell folate than women with normal hearing.

Absorption: The ileum is the major site of absorption of vitamin $B^{12}$ where its intestinal absorption is facilitated by two receptors and two transporters.

Pharmacokinetics: In nature, vitamin $B^{12}$ is only exceptionally met in its free form. It is almost always associated with a binder. Alimentary vitamin $B^{12}$ released from its protein complexes by culinary preparation and gastric secretions, is combined with haptocorrin. In the duodenum, haptocorrin is partially degraded by pancreatic enzymes and intraluminal pH and $B^{12}$ is attached to intrinsic factor for transfer. This combination of the vitamin can then be "caught" by the ileal receptor.

Vitamin D (calciferol)

Otosclerosis is a bone dysplasia limited to the otic capsule causing abnormal resorption and redeposition of bone. The existence of the entity "pure labyrinthine otosclerosis" or "cochlear otosclerosis" is not accepted by all authors; however, there is clinical and histologic evidence to support the existence of a progressive SNHL due to otospongiotic-otosclerotic lesions of the labyrinthine.

A number of authors confirm that vitamin D deficiency with its associated otosclerosis is one of the etiologies of PSNHL, although at least one study was not supportive of this view.

Treatment with vitamin D should prevent progressive hearing loss relating to otosclerosis and may in some cases improve hearing, which may be partly reversible. As an example, the degree of bone atrophy was quantitatively assessed by microdensitometry (MD) in 56 patients with senile deafness. Biochemical examinations were also made leading to a conclusion that abnormal bone metabolism is a factor in some patients with senile deafness. After treatment with an active vitamin D preparation (1 alpha-(OH)D3) at 1 microgram/day for 6 to 10 months, 12 patients suspected of having abnormal bone metabolism had hearing improvement in six ears (four patients).

Zinc ($Zn^{2+}$)

$Zn^{2+}$ deficiency is one cause of presbycusis. $Zn^{2+}$ supplementation in patients who are marginally $Zn^{2+}$ deficient, results in reduction of tinnitus and SNHL in about one-third of those who are elderly adults. While $Zn^{2+}$ supplementation may be useful in improving hearing loss, it must be used with care since this element is a neural transmitter and its use in excess can result in excitotoxicity.

Copper/zinc superoxide dismutase ($Cu/Zn^{2+}$ SOD) is a first-line defense against free radical damage in the cochlea and other tissues. Studies indicate that $Cu/Zn^{2+}$ SOD deficiencies increase the vulnerability of the cochlea to damage associated with normal aging, presumably through metabolic pathways involving the superoxide radical.

Glutamatergic receptors, as exist in the neural pathway related to hearing are vulnerable to excitotoxicity. In some circumstances, an excess of $Ca^{2+}$ influx alters neuronal metabolism and may become lethal for the cell. Two divalent cations, $Mg^{2+}$ and $Zn^{2+}$, have inhibitory effects on the involved NMDA receptors. $Mg^{2+}$ exerts a voltage-dependent block of the NMDA calcium channel, whereas $Zn^{2+}$ exerts a voltage-independent NMDA block. (Melatonin also has inhibitory effects on the NMDA receptor. In the rat, iontophoresis of melatonin, $Mg^{2+}$ and $Zn^{2+}$ produce a potent attenuation of the excitatory response of the cortical striatum, although the latency of the effect of melatonin was longer than those of $Mg^{2+}$ and $Zn^{2+}$. When these cations were simultaneously delivered with melatonin, additive inhibitory effects were recorded. These observations suggest that the inhibitory effects produced by the two cations and by melatonin are produced via different processes. The inhibitory role of melatonin on the NMDA receptor activity appears to be exclusive of a direct action on the NMDA calcium channel.

Absorption: Absorption of $Zn^{+2}$ ranges from 40 to 86%. About 37% of ingested $Zn^{+2}$ enters the plasma and gastrointestinal absorption is essentially completed by 4 hours. The duodenum and ileum are important sites for rapid $Zn^{30\ 2}$ absorption. A continuous, slower absorption of $Zn^{+2}$ may take place in the jejunum while the stomach, cecum and colon appear to be insignificant sites of absorption.

Pharmacokinetics: Mean plasma $Zn^{+2}$ increases only 37% above pre-load levels in face of an 11-fold increase in intake.

DETAILED DESCRIPTION OF THE INVENTION AND PREFERRED EMBODIMENTS

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition, which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

"Vasoconstriction" is the reduction of the cross section of a blood vessel lumen, inhibiting the free flow of blood through the vessel. Vasoconstriction can arise from vasospasm, deposits on or in the lumen wall or from the thickening of the wall material due to excessive growth or proliferation of one or more of the wall layers.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

L-ARGININE may be included in this invention as a free base or combined with the metallic cations contemplated by this invention —$Mg^{+2}$, $Cu^{+2}$ or $Zn^{+2}$- as metal L-arginine complexes which have the following formula:

$$[Arg]MX$$

wherein,
a. Arg is the amino acid L-arginine or bis-L,arginine;
b. M is a metal ion taken from, $Mg^{+2}$, $Cu^{+2}$ or $Zn^{+2}$:
c. X is an anion taken from the group including hydroxides, halides, sulfates, acetates, ascorbates or bis-ascorbic acid salts.

N-ACETYL-CYSTEINE (NAC), mercaptopropionylglycine (MPG) or L-2-oxothiazolidine-4-carboxylate (OTC) may be included in this invention as a free base or combined with the metallic cations contemplated by this invention —$Mg^{+2}$, $Cu^{+2}$ or $Zn^{+2}$-as metal complexes which have the following formula:

$$[A]MX$$

wherein,
a. A is cysteine, acetylcysteine, NAC, MPG or OTC;
b. M is a metal ion taken from the metallic cations contemplated by this invention: $Mg^{+2}$, $Cu^{+2}$ or $Zn^{+2}$;
c. X is an anion taken from the group including hydroxides, halides, sulfates, phosphates, acetates, ascorbates or bis-ascorbic acid salts.

alpha-LIPOIC ACID (LA) or thioctic acid (TA) may be included in this invention as a free base or combined with the metallic cations contemplated by this invention; $Mg^{+2}$, $Cu^{+2}$, $Zn^{+2}$ or $Se^{+2}$ as metal alpha-lipoic acid or thioctic acid complexes which have the following formula:

$$[A]MX$$

wherein,
a. A is LA or TA;
b. M is a metal ion taken from, $Mg^{+2}$, $Cu^{+2}$, $Zn^{+2}$ or selenium ($Se^{+2}$);
c. X is an anion taken from the group including hydroxides, halides, sulfates, phosphates, acetates, ascorbates or bis-ascorbic acid salts.

or $$[A]_2MX$$

wherein,
a. A is LA or TA,
b. M is a metal ion taken from $Mg^{+2}$, $Cu^{+2}$, $Zn^{+2}$ or $Se^{+2}$;

c. X is an anion taken from the group including hydroxides, halides, sulfates, phosphates, acetates or ascorbates or bis-ascorbic acid salts.

L-ARGININE. N-ACETYL-CYSTEINE, TAURINE and alpha-LIPOIC ACID and metals of this invention; $Mg^{+2}$, $Cu^{+2}$, $Zn^{+2}$ or $Se+^2$ may also be included as bi-amide complexes in formulae of this invention with the following structure:

[A]MX wherein,
a. A is 2,N-thioctylarginine (2NTA), 2,N-thioctylcysteine (2NTCy), or 2,N-thioctyltaurine (2NTT);
b. M is a metal ion taken from $Mg^{+2}$, $Cu^{+2}$, $Zn^{+2}$ or $Se^{+2}$;
c. X is an anion taken from the group including hydroxides, halides, sulfates, phosphates, acetates or ascorbates or bis-ascorbic acid salts, or

[A]$_2$MX wherein,
a. A is 2,N-thioctylarginine (2NTA), 2,N-thioctylcysteine (2NTCy), or 2,N-thioctyltatrine (2NTT);
b. M is a metal ion taken from $Mg^{+2}$, $Cu^{+2}$, $Zn^{+2}$ or $Se^{+2}$;
c. X is an anion taken from the group including hydroxides, halides, sulfates, phosphates, acetates or ascorbates or bis-ascorbic acid salts.

TAURINE may be used in this invention in its free forms or complexed or both. Absorption characteristics and pharmacokinetics are described in the "Solubility and Gastrointestinal Absorption Characteristics of the Components" (see above).

MAGNESIUM is present either as $Mg^{+2}$ salts or $Mg^{+2}$ complexes that release magnesium ion when ingested, or both. Examples of salts of $Mg^{+2}$ that can be used in this invention are acetate, acetyl-cysteinate, arginate, ascorbate, lipoate, malate, oxide, stearate, sulfate and taurate. As an example of kinetics after ingestion, magnesium ascorbate is soluble in gastric fluid and the respective components are absorbed in the gastrointestinal tract. The ascorbate radical serves as an adequate source of vitamin C by conversion to ascorbic acid upon exposure to hydrochloric acid in the gastric fluid, while the magnesium ion is converted to soluble magnesium chloride. The satisfactory water solubility of magnesium ascorbate provides for a diffusional gradient of $Mg^{+2}$ in the upper small intestine where some passive absorption of $Mg^{+2}$ occurs. Magnesium oxide is converted to magnesium chloride in the acid environment of the stomach and offers the advantage of high ionic magnesium content, since 60% by weight of the magnesium oxide molecule is $Mg^{+2}$. Magnesium stearate is useful as a lubricant when compressing the composition into tablets, in addition to its use as a minor $Mg^{+2}$ source. Preferred $Mg^{+2}$ sources include magnesium ascorbate, magnesium taurate, magnesium oxide or one of the complexes described previously.

ZINC is present either as $Zn^{+2}$ salts or $Zn^{+2}$ complexes that release $Zn^{+2}$ when ingested, or both. Absorption and pharmacokinetics are described above. Examples of salts of $Zn^{+2}$ that can be used in this invention are acetate, arginate, lipoate, sulfate, and taurate. Preferred $Zn^{+2}$ sources include zinc acetate, zinc taurate or one the complexes described previously.

SELENIUM is present either as $Se^{+2}$ salts or $Se^{+2}$ complexes that release selenium ion when ingested, or both. Absorption and pharmacokinetics are described above. Examples of salts of $Se^{+2}$ that can be used in this invention are acetate, arginate, lipoate, sulfate, and taurate. Preferred $Se^{+2}$ sources are L-selenomethionine, selenium from yeast or from the one of the complexes described previously.

CHROMIUM is present as $Cr^{+3}$ salts release chromium ion when ingested. Absorption and pharmacokinetics are described above. Preferred $Cr^{+3}$ sources include chromium tripicolinate or chromium binicotinate.

VANADIUM is present as vanadium ($V^{2+}$ to $V^{5+}$) salts and release vanadium ion when ingested. Absorption and pharmacokinetics are described above. Preferred vanadium sources include vanadyl sulfate or organic vanadium compounds, such as bis(maltolato)oxovanadium(IV).

D, alpha-TOCOPHEROL and its analogs and esters are D, alpha-tocopherol, D, alpha-tocopherol acid succinate, D, alpha-tocopherol nicotinate and D, alpha-tocopherol acetate. A particularly preferred form of vitamin E is D, alpha-tocopherol acid succinate or microencapsulated D, alpha-tocopherol nicotinate, especially for preparations in tablet form. The gastrointestinal absorption of dietary D, alpha-tocopherol is bile salt dependent and therefore is somewhat also dependent upon the simultaneous digestion and absorption of fat. The presence of dietary taurine, involved in the conversion of cholic acid to dexycholic acid in the gut, enhances D, alpha-tocopherol absorption. In these respects D, alpha-tocopherol absorption may be similar to that of vitamin A and the site of major vitamin A absorption is the proximal small intestine.

ASCORBATE is present either as ascorbic acid, metalloascorbate salts or complexes of ascorbate, or all of these. Examples of metallic salts of ascorbate that can be used in this invention are $Mg^{+2}$, $Cu^{+2}$ or $Zn^{+2}$. Absorption and pharmacokinetics are described above.

GINGKOLIDES (EGB), MELATONIN, UBIQUINONE and the B VITAMINS are present within this invention in their free forms. Absorption and pharmacokinetics are described above.

A slower, more sustained release of the active agents can be achieved by placing the active agents in one or more delivery vehicles that inherently retard the release rate. Examples of such delivery vehicles include polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774

("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

In certain embodiments of the invention, the dosage form is a substantially homogeneous single layer tablet that releases all of its components into the stomach upon ingestion (see below). In some embodiments a sustained dosage form is used and in others both dosage forms are combined into a bilayer tablet. Examples of the preferred ranges for components in each layer are shown in Table I.

TABLE I

| Component | Dosages in milligrams | | % in Bilayer | |
|---|---|---|---|---|
| | Preferred | Most Preferred | Immed/Sustain | |
| Ascorbate | 75 to 3125 | 250 to 1250 | 50% | 50% |
| Calciferol | 30 to 1500 | 100 to 600 | 100% | |
| Carotene, beta | 30 to 1500 | 100 to 600 | 100% | |
| Chromium | 0.01 to 0.63 | 0.03 to 0.25 | 100% | |
| CoQ10 | 4.5 to 225 | 15 to 90 | 50% | 50% |
| Cyanocobalamin | 0.0006 to 0.010 | 0.002 to 0.004 | 100% | |
| Folate, Tetrahydro | 0.03 to 2.0 | 0.10 to 0.80 | 100% | |
| Ginkgo biloba | 7.5 to 250 | 25 to 100 | 50% | 50% |
| Glutathione | 30 to 1500 | 100 to 600 | 100% | |
| L-Arginine | 75 to 6250 | 250 to 2500 | 75% | 25% |
| Lipoate | 30 to 1500 | 100 to 600 | 50% | 50% |
| Magnesium | 30 to 1000 | 100 to 400 | 40% | 60% |
| Melatonin | 0.15 to 7.5 | 0.5 to 3 | 40% | 60% |
| N-Acetyl-L-Cysteine | 78 to 3900 | 200 to 1200 | 75% | 25% |
| Nicotinamide | 3.0 to 1500 | 10 to 150 | 25% | 75% |
| Pyridoxine | 0.3 to 15 | 1.0 to 6.0 | 100% | |
| Riboflavin | 3.6 to 188 | 12 to 75 | 50% | 50% |
| Selenium | 0.015 to 0.75 | 0.05 to 0.3 | 100% | |
| Taurine | 75 to 3125 | 250 to 1250 | 75% | 25% |
| Tocopherol, D alpha | 15 to 1600 | 50 to 800 | 100% | |
| Vanadium | 7.5 to 375 | 25 to 150 | 100% | |
| Zinc | 1.5 to 80 | 5 to 32 | 25% | 75% |

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquids, emulsions, tablets, transmembrane delivery systems, electrophoretic delivery systems and capsules.

The dosage forms of this invention can be formulated for administration at rates of two or more unit dosage forms per day. Tableted unit dosage forms to be taken three to four times per day are preferred.

The following example is offered for purposes of illustration only.

EXAMPLE I

A single layer tablet, substantially homogenous in composition, which will disintegrate upon ingestion to provide simultaneous accessibility to all components, is prepared with the following composition:

TABLE II

| FOR RELEASE IN THE STOMACH | | 100% % of formula |
|---|---|---|
| $Mg(C_6H_7O_6)_2$ | Magnesium L-Ascorbate | 16.64% |
| $Mg(C_5H_9NO_3S)_2$ | Magnesium L-Acetylcysteine | 20.90% |
| $C_8H_{12}O_2S_2$ | Magnesium Lipoate | 6.18% |
| MgO | Magnesium Oxide | 12.64% |
| $C_{35}H_{53}NO_3$ | D a-Tocopherol Nicotinate | 17.15% |
| $C_{19}H_{19}N_7O_6$ | Folic acid | 0.012% |
| $C_5H_{11}NO_2Se$ | L-Selenomethionine | 0.007% |
| $C_{17}H_{20}N_4O_6$ | Riboflavin | 0.39% |
| $Mg(C_{18}H_{35}O_2)_2$ | Magnesium Stearate | 0.77% |
| . . . | Starch | 25.29% |

Methods of Administration and Types of Utility

The compositions and dosage forms of the invention arc useful for treating conditions commonly associated with hearing loss and tinnitus. The carefully chosen active ingredients of the invention act in a well-defined and complementary biochemical partnership to ensure that conditions of potential vascular risk are reduced in these patients. The resulting improvement in systemic and VIIIth nerve vascular health, especially in vascular endothelial health, maximizes the potential for avoiding hearing loss and deafness because of neglected, unrecognized or unappreciated ocular vascular inadequacy. The age group most commonly first diagnosed with hearing loss and tinnitus also is the age group moving into the physiological arena of reduced cellular efficiency secondary to age; at the same time it faces a concomitant increasing incidence of generalized vascular disability and associated chronic disease (e.g., diabetes mellitus, hypertension, hyperlipidosis, hyperinsulinemia). Many of the latter pathologies are associated with progressively widespread and worsening vascular health, a situation that threatens not only hearing but overall health.

By positively influencing the NO/ET-1 balance, reducing adverse homocysteine effects, modulating a controlled reduction in $Ca^{+2}$ cellular inflow via physiological calcium channel blockade, reducing platelet aggregation, lowering microviscosity and improving vascular laminar fluid dynamics, reducing the inflammatory risks associated with local free radicals such as hydroxyls and limiting the rate the oxidation of low-density lipids, the invention provides significant protection for patients. In performing these tasks, it positively influences conditions which otherwise represent risks associated with sensorineural hearing loss and tinnitus.

Epidemiological studies have confirmed repeatedly that inadequate dietary intake of $Mg^{+2}$, ascorbate and folic acid, among others, is common in the general, apparently healthy public and is especially rampant in alcoholics, institutionalized patients, cigarette smokers and the elderly. Other patients have disturbances of reduced absorption or abnormal loss of these and other critical biofactors (e.g., hypochlorhydria, diabetes mellitus, hyperinsulinemia, renal pathology, small or large bowel pathology, etc.) Another subset of patients suffers from a variety of primary diseases that create an underlying foundation of vascular dysfunction, which is worsened by coexistent deficiencies (e.g., essential hypertension, congenital dyslipogenesis, aging, diabetes mellitus type 1 or type 2, etc.) The distribution of patients at risk of hearing loss among any of the above groups is no less than in the general public and the passage of time subjects everyone to the debilitations of aging. The invention is especially useful in reducing the risks of hann associated with those various conditions of vascular dysfunction congruent with these events. While it should be expected that an improvement in general vascular health would be universally beneficial to all of these clinical groups, this invention focuses upon reducing conditions of risk or failing function associated with hearing loss.

The foregoing is offered primarily for purposes of illustration. It will be readily apparent to those skilled in the art that the proportions, materials, formulation procedures, administration protocols and other parameters of this invention may be farther modified or substituted in various ways without departing from the spirit and scope of the invention.

We claim:

1. A unit dosage form for the amelioration of adverse conditions or functions associated with hearing loss or tinnitus comprising as active ingredients:
   (a) magnesium,
   (b) D, alpha-tocopherol,
   (c) folate,
   (d) a thiol-containing glutathione-increasing agent,
   (e) selenium,
   (f) riboflavin,
   (g) ascorbate, and
   (h) zinc.

2. The unit dosage form of claim 1 in which:
   (a) said magnesium is in the form of magnesium oxide in an amount ranging from about 60 mg to about 2500 mg and magnesium lipoate in an amount ranging from about 30 mg to about 1500 mg,
   (b) said alpha-tocopherol is in the form of D, alpha-tocopherol nicotinate in an amount ranging from about 85 mg to about 3500 mg,
   (c) said folate is present in an amount ranging from about 0.03 mg to about 2.0 mg,
   (d) said thiol-containing glutathione-increasing agent is magnesium L-acetyl cysteine in an amount ranging from about 80 mg to about 4000 mg,
   (e) said selenium is in the form of selenomethionine in an amount ranging from about 0.04 to about 1.0 mg,
   (f) said riboflavin is in an amount of about 3.6 mg to about 188 mg,
   (g) said ascorbate is in the form of magnesium ascorbate in an amount ranging from about 80 mg to about 4000 mg, and
   (h) said zinc is in the form of zinc picolinate in an amount ranging from about 7.1 mg to about 500 mg.

3. The unit dosage form of claim 1 in which said active ingredients are formulated as a substantially homogeneous tablet that releases all of said active ingredients into the stomach upon ingestion and contact with gastric fluid.

4. The unit dosage form of claim 2 further comprising as active ingredients L-arginine in an amount ranging from about 75 mg to about 6300 mg and pyridoxine in an amount ranging from about 0.3 mg to about 15 mg.

5. The unit dosage form of claim 4 further comprising as active ingredients taurate in the form of magnesium taurate, in an amount ranging from about 75 mg to about 3100 mg, melatonin in an amount ranging from about 0.15 mg to about 7.5 mg and CoQ10 in an amount ranging from about 4.5 mg to about 225 mg.

6. A unit dosage form for the amelioration of adverse conditions giving rise to hearing loss and tinnitus, said unit dosage form comprising as active ingredients:
   a thiol-containing glutathione-increasing agent having the formula $R_nMX$ in which:
   R is a member selected from the group consisting of N-acetyl-L-cysteine, L-2-oxothiazolidine-4-carboxylate, and N-2(-mercaptopropionyl)-glycine,
   n is 1 or 2,
   M is a member selected from the group consisting of $Mg^{+2}$, $Cu^{+2}$, $Zn^{+2}$, and $Se^{+2}$, and
   X is a member selected from the group consisting of hydroxide, halide, sulfate, acetate, ascorbate, and bis-ascorbate.

7. The unit dosage form of claim 2 in which said zinc is in the form of zinc dinicotinate.

8. The unit dosage form of claim 2 in which said zinc is in the form of zinc ascorbate and is present in an amount ranging from about 9.5 mg to about 500 mg.

9. The unit dosage form of claim 2 in which said zinc is in the form of zinc L-acetylcysteinate and is present in an amount ranging from about 9 mg to about 480 mg.

10. The unit dosage form of claim 5 further comprising as active ingredients chromium in an amount ranging from about 0.1 mg to about 0.63 mg, cyanocobalamine in an amount ranging from about 0.0006 mg to about 0.01 mg and vanadium in an amount ranging from about 7.4 mg to about 375 mg.

11. The unit dosage form of claim 10, further comprising as active ingredients biotin in an amount ranging from about 0.1 mg to about 0.20 mg, beta carotene in an amount ranging from about 30 mg to about 1500 mg, calciferol in an amount ranging from about 100 mg to about 600 mg and Gingko biloba in an amount ranging from about 7.5 mg to about 250 mg.

12. A unit dosage form for the amelioration of adverse conditions giving rise to hearing loss and tinnitus, said unit dosage form comprising as active ingredients:
   (a) magnesium,
   (b) copper,
   (c) zinc, and
   (d) selenium,
   at least one of which is in the form of a complex having the formula $R_nMX$ in which:
   R is a member selected from the group consisting of 2,N-thioctylcysteine, and 2,N-thioctyltaurine,
   n is 1 or 2,
   M is a member selected from the group consisting of $Mg^{+2}$, $Cu^{+2}$, $Zn^{+2}$, and $Se^{+2}$, and
   X is a member selected from the group consisting of hydroxide, halide, sulfate, acetate, ascorbate, and bis-ascorbate.

13. A layered tablet for the amelioration of adverse conditions associated with hearing loss and conditions giving rise thereto, said layered tablet comprising an immediate-release layer and a sustained-release layer, and comprising the following as active ingredients distributed between said immediate-release layer and said sustained-release layer in the following approximate proportions expressed as relative weight percents:

|  | Immediate-Release Layer | Sustained-Release Layer |
| --- | --- | --- |
| Magnesium | 40–60% | balance |
| Ascorbate | 100% | |
| alpha, tocopherol | 100% | |
| alpha, lipoic acid | 40–60% | balance |
| L-arginine | 40–60% | balance |
| beta, carotene | | 100% |
| Copper | 100% | |
| CoQ10 | 40–60% | balance |
| Chromium | | 100% |
| Nicotinamide | 100% | |
| Glutathione-increasing agent | 40–60% | balance |

14. A layered tablet for use as an oral dosage form, said layered tablet comprising an immediate-release layer and a sustained-release layer, and comprising the following as active ingredients distributed between said immediate-release layer and said sustained-release layer in the following approximate proportions expressed as relative weight percents:

|  | Immediate-Release Layer | Sustained-Release Layer |
| --- | --- | --- |
| Magnesium | 40–60% | balance |
| Selenium | 100% | |
| Vitamin D | 40–60% | balance |
| L, arginine | 40–60% | balance |
| Taurine | 40–60% | balance |
| Zinc | 100% | |
| Folic acid | 100% | |
| Gingko biloba | | 100% |
| Melatonin | 100% | |

* * * * *